US008486166B2

(12) United States Patent
Yahagi et al.

(10) Patent No.: US 8,486,166 B2
(45) Date of Patent: Jul. 16, 2013

(54) FUEL REFORMING APPARATUS

(75) Inventors: Hideo Yahagi, Gotemba (JP); Isamu Nakada, Mishima (JP); Keiichiro Aoki, Numazu (JP); Takanori Sasaki, Susono (JP)

(73) Assignee: Toyota Jidosha Kabushiki Kaisha, Toyota-shi (JP)

( * ) Notice: Subject to any disclaimer, the term of this patent is extended or adjusted under 35 U.S.C. 154(b) by 654 days.

(21) Appl. No.: 12/744,691

(22) PCT Filed: Jan. 26, 2009

(86) PCT No.: PCT/JP2009/051674
§ 371 (c)(1),
(2), (4) Date: May 26, 2010

(87) PCT Pub. No.: WO2009/107454
PCT Pub. Date: Sep. 3, 2009

(65) Prior Publication Data
US 2010/0300382 A1 Dec. 2, 2010

(30) Foreign Application Priority Data
Feb. 27, 2008 (JP) ................................. 2008-046398

(51) Int. Cl.
*B01J 7/00* (2006.01)
(52) U.S. Cl.
USPC ............ 48/61; 48/127.9; 48/127.1; 48/197 R; 48/198.6; 48/198.7; 48/214 R; 48/215; 48/214 A; 123/688; 123/693; 123/674; 123/3; 60/274; 60/276; 422/105; 422/110; 422/111; 422/625; 422/630; 422/633
(58) Field of Classification Search
USPC ............ 48/61, 127.1, 127.9, 197 R; 422/625, 422/630
See application file for complete search history.

(56) References Cited

U.S. PATENT DOCUMENTS

| 5,472,580 | A | 12/1995 | Kennard, III et al. |
| 6,887,286 | B1 * | 5/2005 | Taki et al. ................... 48/197 R |
| 6,997,142 | B2 | 2/2006 | Wakao et al. |
| 2001/0007192 | A1 | 7/2001 | Suzuki et al. |
| 2004/0005494 | A1 * | 1/2004 | Drake et al. ..................... 429/38 |
| 2004/0068933 | A1 * | 4/2004 | Nakamura et al. ........... 48/127.9 |
| 2008/0202449 | A1 | 8/2008 | Shimada et al. |
| 2008/0243356 | A1 * | 10/2008 | Kang et al. .................... 701/102 |
| 2009/0019832 | A1 * | 1/2009 | Katoh ............................. 60/276 |

FOREIGN PATENT DOCUMENTS
| DE | 10 2005 043 414 | 3/2007 |
| FR | 2 898 682 | 9/2007 |

(Continued)

OTHER PUBLICATIONS

Japanese Office Action issued Dec. 20, 2011, in Patent Application No. 2008-046398.

*Primary Examiner* — Kaity V. Handal
(74) *Attorney, Agent, or Firm* — Oblon, Spivak, McClelland, Maier & Neustadt, L.L.P.

(57) ABSTRACT

Fuel reforming catalysts 28 generate a hydrogen-containing reformed gas when they come into contact with exhaust gas that contains a reforming fuel. Upstream and downstream air-fuel ratio sensors 58, 60 are respectively installed upstream and downstream of the fuel reforming catalysts 28. The upstream air-fuel ratio sensor 58 outputs a upstream sensor signal in accordance with oxygen concentration. The downstream air-fuel ratio sensor 60 outputs a downstream sensor signal in accordance with oxygen concentration and hydrogen concentration by using zirconia's oxygen detection capability and a change of a diffusion layer's hydrogen-concentration-dependent oxygen detection capability. An ECU 50 detects the hydrogen concentration without being affected by the oxygen concentration through the use of the upstream sensor signal in which only the oxygen concentration is reflected and the downstream sensor signal in which the oxygen concentration and hydrogen concentration are reflected. This makes it possible to establish a hydrogen concentration detection system with the common air-fuel ratio sensors 58, 60.

18 Claims, 9 Drawing Sheets

FOREIGN PATENT DOCUMENTS

| | | |
|---|---|---|
| JP | 5 264501 | 10/1993 |
| JP | 2003 4698 | 1/2003 |
| JP | 2004-251273 | 9/2004 |
| JP | 2005 247672 | 9/2005 |
| JP | 2006-29296 | 2/2006 |
| JP | 2007 113420 | 5/2007 |
| JP | 2007 113421 | 5/2007 |
| JP | 2007-231779 | 9/2007 |
| WO | 2007 057720 | 5/2007 |
| WO | 2008 016070 | 2/2008 |

* cited by examiner

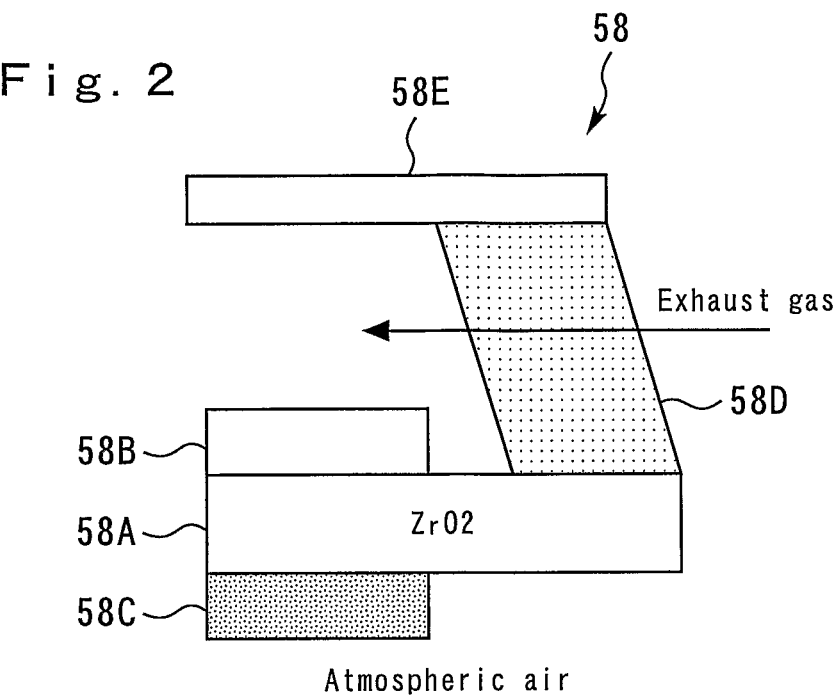
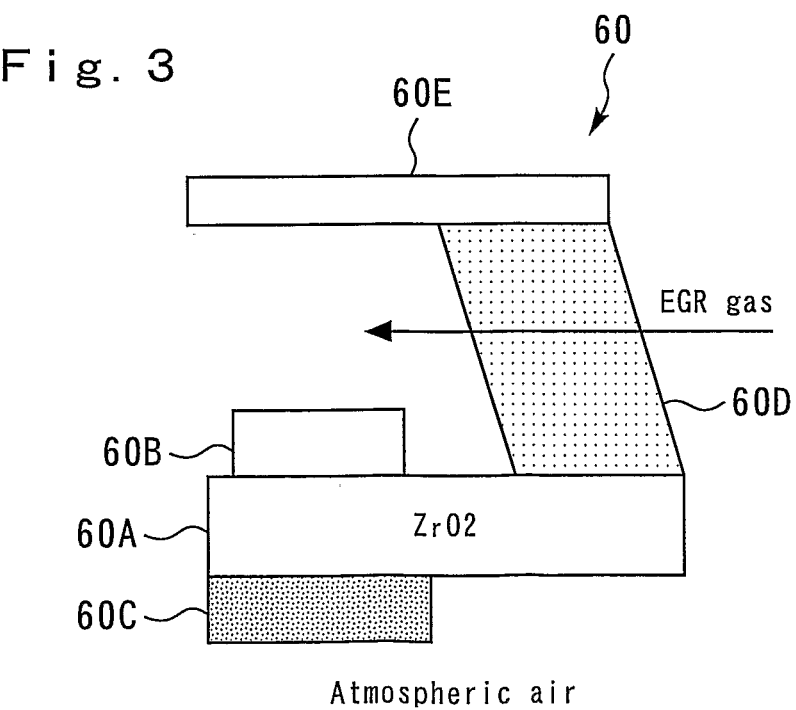

FUEL REFORMING APPARATUS

TECHNICAL FIELD

The present invention relates to a fuel reforming apparatus that is preferably used to generate a combustible gas from a reforming fuel with the aid of a fuel reforming catalyst.

BACKGROUND ART

There is a conventionally known internal combustion engine with a fuel reforming apparatus as disclosed, for instance, in Patent Document 1 (JP-A-2007-113421). Such a prior art fuel reforming apparatus includes a fuel reforming catalyst that generates a hydrogen-containing combustible gas by reforming a gas containing a reforming fuel and oxygen.

While the fuel reforming catalyst is active, it can generate a combustible gas that contains hydrogen and carbon monoxide. However, while it is inactive, it cannot generate a combustible gas having a sufficiently high concentration. Therefore, the prior art fuel reforming apparatus is configured so that a hydrogen or carbon monoxide concentration sensor is positioned downstream of the fuel reforming catalyst. Further, when the result of detection by the concentration sensor indicates that a combustible gas having a sufficiently high concentration is generated, the prior art fuel reforming apparatus supplies the combustible gas to an intake path of the internal combustion engine.

Including the above-mentioned document, the applicant is aware of the following document as a related art of the present invention.
[Patent Document 1] JP-A-2007-113421

DISCLOSURE OF INVENTION

Meanwhile, the prior art fuel reforming apparatus described above is configured so as to use the concentration sensor that detects the concentration of hydrogen or carbon monoxide. The concentrations of hydrogen and carbon monoxide correlate to the amount of combustible gas generation. Therefore, the amount of combustible gas generation can be accurately detected when concentration detection is accurately achieved.

However, a small-size, inexpensive concentration sensor that could be mounted in the prior art fuel reforming apparatus does not readily achieve high detection accuracy. Further, when an operation is performed to detect the concentration of hydrogen, oxygen and other components contained in the combustible gas may affect the detection operation, resulting in a decrease in detection accuracy.

The present invention has been made to solve the above problem. It is an object of the present invention to provide a fuel reforming apparatus that is capable of implementing a small-size, inexpensive, hydrogen concentration sensor and accurately detecting the amount of combustible gas generation even when a generated combustible gas contains components other than hydrogen.

The above object is achieved by a fuel reforming apparatus which comprise a fuel reforming catalyst which is positioned in a flow path of a gaseous material containing a reforming fuel and used to generate a hydrogen-containing combustible gas from the reforming fuel.

The fuel reforming apparatus comprise an upstream air-fuel ratio sensor which is positioned upstream of the fuel reforming catalyst with respect to the flow direction of the gaseous material and used to output an upstream sensor signal representing the concentration of oxygen in the gaseous material.

The fuel reforming apparatus comprise a downstream air-fuel ratio sensor which is positioned downstream of the fuel reforming catalyst with respect to the flow direction of the gaseous material and used to output a downstream sensor signal representing the concentrations of oxygen and hydrogen in the gaseous material.

And the fuel reforming apparatus comprise hydrogen concentration detection means which uses the upstream sensor signal and the downstream sensor signal to detect the concentration of hydrogen in the gaseous material at a position downstream of the fuel reforming catalyst.

In a second aspect of the present invention, the fuel reforming apparatus according to the first aspect of the present invention, wherein the hydrogen concentration detection means may be include signal correction means for correcting the influence of the oxygen concentration, which is contained in the downstream sensor signal, in accordance with the upstream sensor signal.

In a third aspect of the present invention, the fuel reforming apparatus according to the second aspect of the present invention, may comprise oxygen concentration calculation means which calculates the oxygen concentration from the upstream sensor signal.

And the fuel reforming apparatus comprise storage means which stores, in advance, characteristic curve data indicative of the relationship between the downstream sensor signal and the hydrogen concentration. And the signal correction means corrects the characteristic curve data in accordance with the oxygen concentration. And the hydrogen concentration detection means uses the corrected characteristic curve data to calculate the hydrogen concentration from the downstream sensor signal.

In a fourth aspect of the present invention, the fuel reforming apparatus according to the third aspect of the present invention, wherein the signal correction means may include zero-point output acquisition means which acquires a value of the downstream sensor signal in accordance with the oxygen concentration when the hydrogen concentration is zero.

And the signal correction means includes change ratio acquisition means which acquires the ratio of a change in the downstream sensor signal to a change in the hydrogen concentration in accordance with the oxygen concentration. And the signal correction means includes characteristic setup means which sets the characteristic curve data at detected oxygen concentration in accordance with the results of acquisition by the zero-point output acquisition means and the change ratio acquisition means.

In a fifth aspect of the present invention, the fuel reforming apparatus according to any one of the first to fourth aspect of the present invention, wherein the downstream air-fuel ratio sensor may have a lower sensitivity than the upstream air-fuel ratio sensor.

In a sixth aspect of the present invention, the fuel reforming apparatus according to any one of the first to fifth aspect of the present invention, wherein the upstream air-fuel ratio sensor and the downstream air-fuel ratio sensor each may include a detection element, which is made of a zirconia-containing material and provided with one side surface and an additional side surface.

And the upstream air-fuel ratio sensor and the downstream air-fuel ratio sensor each include two electrodes, which are mounted respectively on one side surface and on the additional side surface of the detection element to face each other with the detection element in between. And the upstream air-fuel ratio sensor and the downstream air-fuel ratio sensor each include limitation means, which is positioned to shield one side surface of the detection element from the gaseous material containing a detection target and limit the rate at which the detection target is supplied to one side surface of the detection element.

In a seventh aspect of the present invention, the fuel reforming apparatus according to the sixth aspect of the present invention, wherein the electrodes of the downstream air-fuel ratio sensor may have a smaller opposing surface area than the electrodes of the upstream air-fuel ratio sensor. And wherein the sensitivity of the downstream air-fuel ratio sensor is lowered in accordance with the opposing surface area difference between the upstream and downstream air-fuel ratio sensors.

In an eighth aspect of the present invention, the fuel reforming apparatus according to the sixth or seventh aspect of the present invention, wherein the limitation means may be a diffusion layer that allows an extraneous gaseous material containing the detection target to pass toward one side surface of the detection element.

And wherein the diffusion layer of the downstream air-fuel ratio sensor has a lower permeability than the diffusion layer of the upstream air-fuel ratio sensor. And wherein the sensitivity of the downstream air-fuel ratio sensor is lowered in accordance with the permeability difference between the upstream and downstream air-fuel ratio sensors.

In a ninth aspect of the present invention, the fuel reforming apparatus according to any one of the first to eighth aspect of the present invention, may further comprise pressure detection means for detecting the pressure of the gaseous material. And the fuel reforming apparatus comprises pressure-dependent correction means for correcting the value of at least either the upstream sensor signal or the downstream sensor signal in accordance with the pressure of the gaseous material.

In a tenth aspect of the present invention, the fuel reforming apparatus according to the ninth aspect of the present invention, wherein the pressure-dependent correction means may make corrections so that the detected concentration of oxygen or hydrogen decreases with an increase in the pressure.

In an eleventh aspect of the present invention, the fuel reforming apparatus according to any one of the first to tenth aspect of the present invention, may further comprise gaseous material supply means which individually supplies an oxygen-free gaseous material and atmospheric air to at least either the upstream air-fuel ratio sensor or the downstream air-fuel ratio sensor.

And the fuel reforming apparatus comprises first oxygen error detection means which detects the amount of deviation between an output signal value of the air-fuel ratio sensor and a predefined zero-point reference value while the oxygen-free gaseous material is supplied to the air-fuel ratio sensor.

And the fuel reforming apparatus comprises second oxygen error detection means which detects the amount of deviation between an output signal value of the air-fuel ratio sensor and a predefined atmospheric air reference value while the atmospheric air is supplied to the air-fuel ratio sensor. And the fuel reforming apparatus comprises oxygen signal calibration means which calibrates the output signal values by using the amounts of deviation from the zero-point reference value and the atmospheric air reference value.

In a twelfth aspect of the present invention, the fuel reforming apparatus according to any one of the first to eleventh aspect of the present invention, may further comprise reforming fuel supply means which supplies the reforming fuel to the fuel reforming catalyst. And the fuel reforming apparatus comprise gaseous material supply means which supplies an oxygen-free gaseous material to the downstream air-fuel ratio sensor.

And the fuel reforming apparatus comprise adjustment means which makes adjustments to place parameters affecting the hydrogen concentration in a predefined error detection state. And the fuel reforming apparatus comprise first hydrogen error detection means which detects the amount of deviation between an output signal value of the downstream air-fuel ratio sensor and a predefined zero-point reference value while the supply of reforming fuel is shut off with the oxygen-free gaseous material supplied to the downstream air-fuel ratio sensor.

And the fuel reforming apparatus comprise second hydrogen error detection means which detects the amount of deviation between an output signal value of the downstream air-fuel ratio sensor and a predefined nonzero-point reference value while the parameters are adjusted and placed in the predefined state with the oxygen-free gaseous material supplied to the downstream air-fuel ratio sensor. And the fuel reforming apparatus comprise hydrogen signal calibration means which calibrates the output signal values by using the amounts of deviation from the zero-point reference value and the nonzero-point reference value.

In a thirteenth aspect of the present invention, the fuel reforming apparatus according to any one of the first to twelfth aspect of the present invention, may further comprise catalyst diagnosis means which makes adjustments to place parameters affecting the hydrogen concentration in a predefined catalyst diagnosis state and compares a detected hydrogen concentration against a predefined diagnosis reference value to run a diagnostic check on the operation of the fuel reforming catalyst.

In a fourteenth aspect of the present invention, the fuel reforming apparatus according to any one of the first to thirteenth aspect of the present invention, wherein the upstream air-fuel ratio sensor is used during air-fuel ratio feedback control to regulate the air-fuel ratio in accordance with the concentration of oxygen in an exhaust gas emitted from an internal combustion engine.

In accordance with the first aspect of the present invention, the air-fuel ratio sensors having a detection element made, for instance, of zirconia ($ZrO_2$) have sensitivity for oxygen concentration detection. Therefore, the upstream air-fuel ratio sensor can output the upstream sensor signal in accordance with the concentration of oxygen in the gaseous material. The downstream air-fuel ratio sensor also has sensitivity for oxygen concentration detection. However, while the fuel reforming catalyst is operating, the gaseous material flowing across the downstream air-fuel ratio sensor contains the combustible gas.

In the above instance, the oxygen detection sensitivity of zirconia is affected by hydrogen existing around the sensors. More specifically, the outputs generated from the air-fuel ratio sensors while hydrogen exists deviate from the outputs generated in a reference state where no hydrogen exists so that the oxygen concentration is lowered (to provide a richer air-fuel ratio). This enables the downstream air-fuel ratio sensor to output the downstream sensor signal in accordance with the concentrations of oxygen and hydrogen in the gaseous material.

Therefore, when the downstream sensor signal is corrected by using the upstream sensor signal, it is possible to eliminate the influence of oxygen concentration from the downstream sensor signal and accurately determine the hydrogen concentration in accordance with the corrected downstream sensor signal. Consequently, the use of two common air-fuel ratio sensors makes it possible to easily and accurately detect the hydrogen concentration and calculate the amount of combustible gas generation with high accuracy in accordance with the result of detection.

As a result, a system for detecting the amount of combustible gas can be implemented by using small-size, inexpensive, air-fuel ratio sensors. This eliminates the necessity of using a dedicated hydrogen concentration sensor or the concentration of carbon monoxide and facilitates system downsizing and cost reduction. Further, the upstream air-fuel ratio sensor can be used to correct the influence of oxygen concentration. This makes it possible to certainly prevent the oxygen concentration from decreasing the accuracy of hydrogen concentration detection and provide consistent detection accuracy.

In accordance with the second aspect of the present invention, the signal correction means can correct the downstream sensor signal by using the upstream sensor signal in which the oxygen concentration is reflected. This makes it possible to eliminate the influence of oxygen concentration from the downstream sensor signal in which the oxygen concentration and hydrogen concentration are reflected. Consequently, the hydrogen concentration can be accurately determined in accordance with the corrected downstream sensor signal.

In accordance with the third aspect of the present invention, the signal correction means can correct the characteristic curve data, which indicates the relationship between the downstream sensor signal and hydrogen concentration, in accordance with the oxygen concentration. Thus, the characteristic curve data represents the relationship between the downstream sensor signal and hydrogen concentration that prevails at detected oxygen concentration. Consequently, the hydrogen concentration calculation means can accurately calculate the hydrogen concentration from the downstream sensor signal by using the characteristic curve data.

In accordance with the fourth aspect of the present invention, the downstream sensor signal linearly varies with the hydrogen concentration when the oxygen concentration is fixed. Therefore, a characteristic curve indicative of the relationship between the downstream sensor signal and hydrogen concentration is linear. The intercept and gradient of the characteristic curve vary with the oxygen concentration. Consequently, the zero-point output acquisition means calculates a zero-point output, which is the intercept of the characteristic curve, that is, the value of the downstream sensor signal prevailing at a hydrogen concentration of zero, in accordance with the oxygen concentration.

Further, the change ratio acquisition means calculates the change ratio, which is the gradient of the characteristic curve, that is, the ratio of a change in the downstream sensor signal to a change in the hydrogen concentration, in accordance with the oxygen concentration. Thus, the characteristic setup means can accurately set the characteristic curve data related to the detected oxygen concentration by using the zero-point output and change ratio. Consequently, the influence of oxygen concentration can be accurately reflected in the characteristic curve data.

In accordance with the fifth aspect of the present invention, the output range of a common air-fuel ratio sensor designed for oxygen concentration detection is not enough to cover the range of hydrogen concentration variation when an attempt is made to detect the hydrogen concentration, which changes the sensor signal to a greater extent than the oxygen concentration. As such being the case, the sensitivity of the downstream air-fuel ratio sensor (the ratio of a change in the sensor signal to a change in concentration) is intentionally decreased to avoid the problem of output range insufficiency.

As a result, the range over which the downstream sensor signal varies with the hydrogen concentration can match the output range of the sensor. This makes it possible to prevent the downstream sensor signal from becoming saturated due to an excessively narrow output range and consistently detect a wide range of hydrogen concentration.

In accordance with the sixth aspect of the present invention, a common air-fuel ratio sensor having a detection element made of zirconia may be used as the upstream air-fuel ratio sensor and downstream air-fuel ratio sensor. Thus, the functionality of zirconia, which causes an ion current to vary with oxygen concentration and hydrogen concentration, can be used to establish a hydrogen concentration detection system with ease.

In accordance with the seventh aspect of the present invention, the two electrodes constituting the downstream air-fuel ratio sensor can have a smaller opposing surface area than the two electrodes constituting the upstream air-fuel ratio sensor. Therefore, the ion current flowing between the electrodes under certain concentration conditions can be reduced by the amount of decrease in the opposing surface area of the electrodes. This makes it possible to reduce the sensitivity of the downstream air-fuel ratio sensor.

In accordance with the eighth aspect of the present invention, the diffusion layer of the downstream air-fuel ratio sensor can have a lower permeability than the diffusion layer of the upstream air-fuel ratio sensor when the former is made, for instance, of a dense material. Thus, the oxygen ions and hydrogen ions to be supplied to the detection element under certain concentration conditions can be reduced in number by the amount of decrease in diffusion layer permeability. This makes it possible to decrease the sensitivity of the downstream air-fuel ratio sensor.

In accordance with the ninth aspect of the present invention, the sensitivity of an air-fuel ratio sensor varies with the pressure of the gaseous material. Therefore, the pressure-dependent correction means corrects a sensor signal by the amount of pressure-dependent change in sensor sensitivity. This makes it possible to eliminate the influence of pressure from the sensor signal. Consequently, even when the pressure of the gaseous material changes, the oxygen concentration and hydrogen concentration can be accurately detected without being affected by such a pressure change.

In accordance with the tenth aspect of the present invention, the higher the pressure of the gaseous material, the larger the number of gaseous material molecules supplied to the detection element of an air-fuel ratio sensor, and thus the higher the sensitivity of the air-fuel ratio sensor. Therefore, the concentration detected by the air-fuel ratio sensor increases with an increase in the pressure of the gaseous material. Consequently, the pressure-dependent correction means makes corrections so that the detected concentration decreases with an increase in the pressure. This makes it possible to counteract the influence of pressure on the detected concentration.

In accordance with the eleventh aspect of the present invention, the gaseous material supply means can easily produce an oxygen-free state and atmospheric air supply state in which an air-fuel ratio sensor output can be calibrated. The first oxygen error detection means can detect the amount of deviation between a sensor signal value and zero-point reference value in the oxygen-free state. Further, the second oxygen error detection means can detect the amount of deviation between the sensor signal value and atmospheric air reference value in a state where atmospheric air having a known oxygen concentration is supplied to an air-fuel ratio sensor.

The output characteristics of the air-fuel ratio sensors are linear with respect to the oxygen concentration. Therefore, the oxygen signal calibration means can accurately calibrate the output characteristics of the sensors with respect to the oxygen concentration by using the amounts of deviation in two different states, namely, the aforementioned oxygen-free state and atmospheric air supply state. Consequently, the oxygen concentration can be continuously detected with high accuracy even when the air-fuel ratio sensors are deteriorated. Further, the accuracy of hydrogen concentration detection can also be increased by increasing the accuracy of oxygen concentration detection.

In accordance with the twelfth aspect of the present invention, the reforming fuel supply means, gaseous material supply means, and adjustment means can be used to easily produce an oxygen-free, hydrogen-free state where sensor output calibration can be effected with respect to the hydrogen concentration and an oxygen-free state where hydrogen having a predefined concentration is supplied. The first hydrogen error detection means can detect the amount of deviation between a sensor signal value and zero-point reference value in the oxygen-free, hydrogen-free state. Further, the second hydrogen error detection means can detect the amount of deviation between a sensor signal value and non-zero-point reference value in the oxygen-free, predefined hydrogen supply state.

The output characteristics of the air-fuel ratio sensors are also linear with respect to the hydrogen concentration. Therefore, the hydrogen signal calibration means can accurately calibrate the output characteristics of the sensors with respect to the hydrogen concentration by using the amounts of deviation in two different states, namely, the aforementioned oxygen-free, hydrogen-free state and oxygen-free, predefined hydrogen supply state. Consequently, the hydrogen concentration can be continuously detected with high accuracy even when the air-fuel ratio sensors are deteriorated.

In accordance with the thirteenth aspect of the present invention, the catalyst diagnosis means can compare a value of a hydrogen concentration detected in the predefined catalyst diagnosis state against the predefined diagnosis reference value. Therefore, the catalyst diagnosis means can run a diagnostic check on the operation of the fuel reforming catalyst in accordance with the amount of hydrogen concentration deviation from the diagnosis reference value. In this instance, a diagnostic check can be accurately performed on the catalyst because the two air-fuel ratio sensors can accurately detect the hydrogen concentration. This makes it possible to certainly grasp, for instance, the deterioration of the fuel reforming catalyst, thereby providing enhanced reliability.

In accordance with the fourteenth aspect of the present invention, an air-fuel ratio sensor used during air-fuel ratio feedback control in an internal combustion engine can double as the upstream air-fuel ratio sensor for hydrogen concentration detection. Therefore, even when the two air-fuel ratio sensors are used for hydrogen concentration detection, it is possible to minimize an increase in the number of sensors and other parts, thereby contributing to further system simplification and cost reduction.

BRIEF DESCRIPTION OF DRAWINGS

FIG. 2 is a cross-sectional view to show the structure of the upstream air-fuel ration sensor.

FIG. 3 is a cross-sectional view to show the structure of the downstream air-fuel ration sensor.

BEST MODE FOR CARRYING OUT THE INVENTION

First Embodiment

Configuration of First Embodiment

Figure 1:
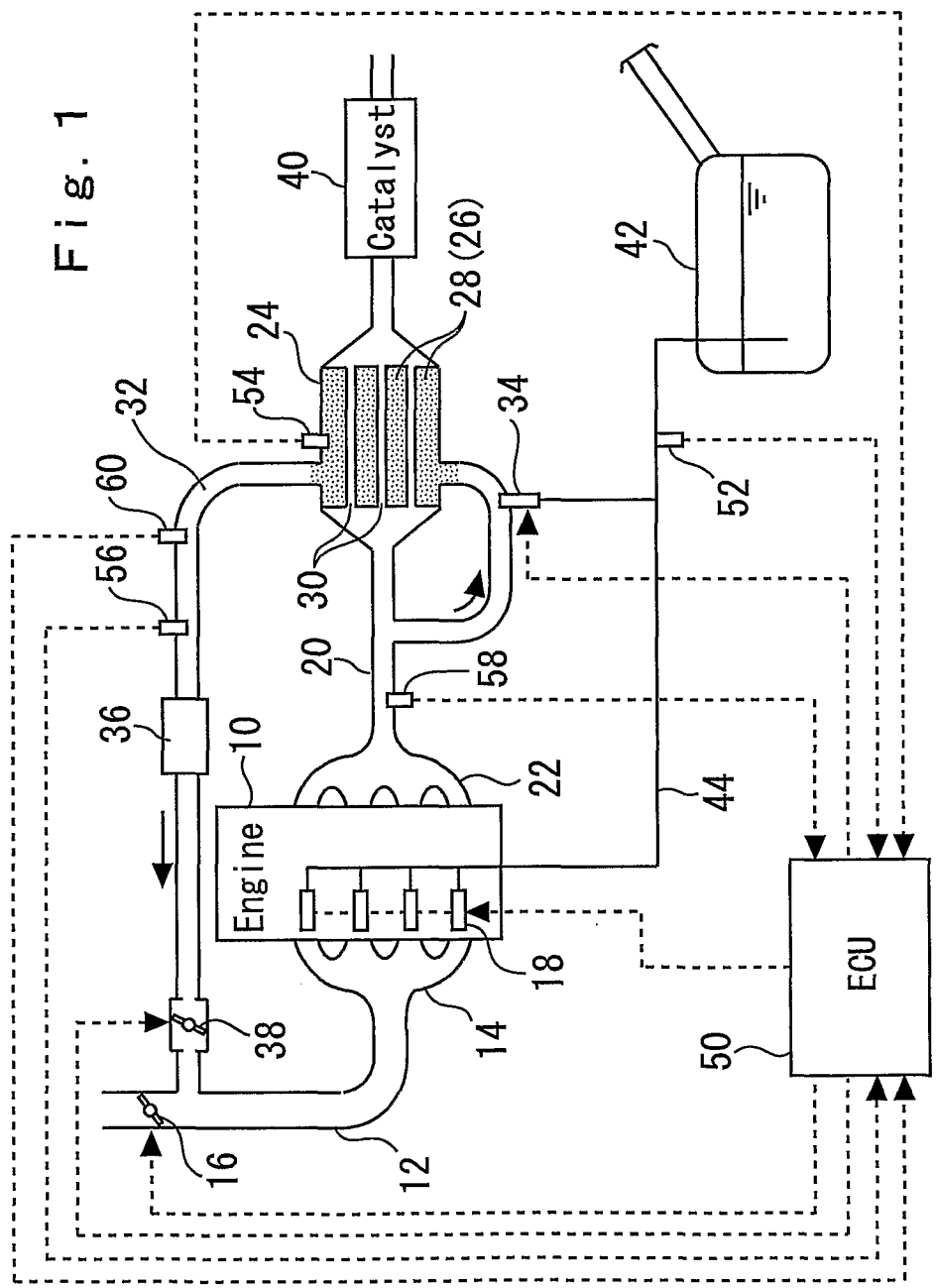
FIG. 1 is an overall view to show the system constitution of a fuel reforming apparatus according the first embodiment.

A first embodiment of the present invention will now be described with reference to FIGS. 1 to 11. FIG. 1 is an overall configuration diagram illustrating the configuration of a system according to the first embodiment. The system according to the present embodiment includes, for instance, a multi-cylinder internal combustion engine 10. This internal combustion engine 10 operates on a fuel mixture of alcohol and gasoline. The present embodiment assumes that a fuel mixture of ethanol and gasoline is used.

An intake pipe 12 of the internal combustion engine 10 is connected to an intake port of each cylinder through an intake manifold 14. An electric throttle valve 16 is installed in the middle of the intake pipe 12 to adjust the amount of intake air. The intake port of each cylinder is provided with a main fuel injection valve 18, which is composed, for instance, of a solenoid valve for fuel injection.

An exhaust pipe 20 of the internal combustion engine 10 is connected to an exhaust port of each cylinder through an exhaust manifold 22. A heat exchanger 24 is installed in the middle of the exhaust pipe 20. A plurality of reforming chambers 26 are formed in the heat exchanger 24 and positioned at intervals. A fuel reforming catalyst 28, which contains metallic materials such as Rh, Pt, Co, Ni, Ru, and Cu, is supported within each of these reforming chambers 26.

An exhaust path 30 is provided in each space between the reforming chambers 26 and shielded from the reforming chambers 26. These exhaust paths 30 are connected to the middle of the exhaust pipe 20. The heat exchanger 24, which is configured as described above, can heat the reforming chambers 26 (fuel reforming catalysts 28) by using the heat of an exhaust gas passing through the exhaust paths 30. When heated in this manner, the fuel reforming catalysts 28 can induce a later-described reforming reaction.

The exhaust pipe 20 is provided with an EGR path 32, which branches off from the exhaust pipe 20 at an upstream end of the heat exchanger 24 and converges with the intake pipe 12. The EGR path 32 is used so that part of the exhaust gas flows back to the intake pipe 12. The reforming chambers 26 of the heat exchanger 24 are connected to the middle of the EGR path 32.

Further, the EGR path 32 is provided with an electromagnetic reforming fuel injection valve 34, which is positioned upstream of the fuel reforming catalysts 28. The reforming fuel injection valve 34 injects fuel (hereinafter referred to as the reforming fuel) into the exhaust gas flowing in the EGR path 32. In this manner, the reforming fuel injection valve 34 constitutes reforming fuel supply means, which supplies the reforming fuel to the fuel reforming catalysts 28.

The EGR path 32 is also provided with a cooler 36, which cools EGR gas, and an electromagnetic flow regulating valve 38. The cooler 36 and flow regulating valve 38 are positioned downstream of the fuel reforming catalysts 28. The flow regulating valve 38 varies the flow rate of the EGR gas that flows back to the intake pipe 12 through the EGR path 32.

In the system configured as described above, part of the exhaust gas flowing in the exhaust pipe 20 flows into the EGR path 32 and receives the supply of the reforming fuel from the reforming fuel injection valve 34. The resulting mixture of the exhaust gas and reforming fuel then flows into the reforming chambers 26 through the EGR path 32 and induces a later-described reforming reaction with the aid of the fuel reforming catalysts 28.

A reformed gas (combustible gas) derived from the reforming reaction serves as the EGR gas that is mixed with the exhaust gas. The EGR gas then flows back into the intake pipe 12 through the EGR path 32 and mixes with intake air. The remaining exhaust gas, which flows in the exhaust pipe 20 but has not flowed into the EGR path 32, passes through the exhaust paths 30 in the heat exchanger 24 to supply heat to the reforming chambers 26. This exhaust gas is then purified by an exhaust purification catalyst 40, which is installed in the exhaust pipe 20 and composed, for instance, of a three-way catalyst, and emitted to the outside.

Meanwhile, the fuel mixture of ethanol and gasoline is stored in a fuel tank 42 for the internal combustion engine 10. The fuel tank 42 is provided with a fuel pump (not shown) that pressurizes fuel in the tank and delivers the pressurized fuel to the outside. A fuel piping 44 is connected to the discharge side of the fuel pump to supply the pumped fuel to each of the fuel injection valves 18, 34.

The system according to the present embodiment also includes an ECU (Electronic Control Unit) 50. The ECU 50 includes a microcomputer having storage circuits such as a ROM and a RAM, and constitutes storage means of the present embodiment. The input end of the ECU 50 is connected to a sensor system, which includes a rotation sensor for detecting the engine rotation speed, an air flow meter for detecting the amount of intake air, a water temperature sensor for detecting the temperature of cooling water, and an accelerator opening sensor for detecting an accelerator opening, and controls the operation of the internal combustion engine 10.

The sensor system also includes a fuel property sensor 52, a temperature sensor 54, a pressure sensor 56, an upstream air-fuel ratio sensor 58, and a downstream air-fuel ratio sensor 60. The fuel property sensor 52 is installed, for instance, in the fuel piping 44 to detect the fuel's mixing ratio between gasoline and alcohol. The temperature sensor 54 is installed, for instance, in the reforming chambers 26 of the heat exchanger 24 to detect the temperature of the fuel reforming catalysts 28 (or the exhaust gas).

The pressure sensor 56 is installed in the EGR path 32 and positioned, for instance, downstream of the heat exchanger 24 (reforming chambers 26). The pressure sensor 56 constitutes pressure detection means, which detects the pressure of the exhaust gas (EGR gas). The upstream air-fuel ratio sensor 58 and the downstream air-fuel ratio sensor 60 will be described later.

The output end of the ECU 50 is connected to various actuators such as the aforementioned throttle valve 16, main fuel injection valve 18, reforming fuel injection valve 34, flow regulating valve 38, and fuel pump. The ECU 50 uses the sensor system to detect the operating status of the internal combustion engine 10 and drives the actuators to exercise operation control.

Operation control, which is mentioned above, is exercised, for instance, to provide normal fuel injection control, air-fuel ratio feedback control, and later-described reforming EGR control. Normal fuel injection control is exercised so that the amount of fuel injected from the main fuel injection valve 18 corresponds, for instance, to the intake air amount. Air-fuel ratio feedback control is exercised so that the amount of fuel injection from the main fuel injection valve 18 increases or decreases in accordance with the air-fuel ratio detected by the upstream air-fuel ratio sensor 58 until the air-fuel ratio of the internal combustion engine agrees with a stoichiometric air-fuel ratio.

(Reforming EGR Control)

The ECU 50 exercises reforming EGR control as described below so that a reformed gas, which is derived from a reforming reaction between the exhaust gas and reforming fuel, flows back into the intake pipe 12 together with the exhaust gas. Reforming EGR control is exercised so as to let the reforming fuel injection valve 34 inject the reforming fuel into the exhaust gas flowing in the EGR path 32 and introduce the resulting mixed gas into the reforming chambers 26.

In the above instance, the ECU 50 determines a proper reforming fuel injection amount (supply amount) in accordance, for instance, with the operating status of the internal combustion engine 10, the concentration of ethanol in fuel, the temperature of the fuel reforming catalysts 28, and the reformed gas generation amount detected by the air-fuel ratio sensors 58, 60.

The fuel reforming catalysts 28 in the reforming chambers 26 then induce a reforming reaction (steam reforming reaction) between ethanol in the mixed gas and steam and carbon dioxide in the exhaust gas. As a result of this steam reforming reaction, hydrogen ($H_2$) and carbon monoxide (CO) are generated as indicated in Equation (1) below:

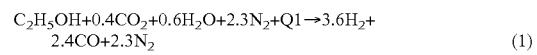

(1)

A reforming reaction also occurs between the gasoline in the mixed gas and the steam and carbon dioxide in the exhaust gas as indicated in Equation (2) below:

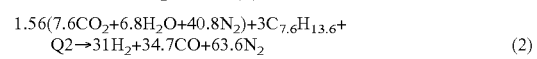

(2)

The calorific value Q1 in Equation (1) and the calorific value Q2 in Equation (2) represent reaction heat that is absorbed by the reforming reactions. Since the reforming reactions are endothermic reactions, the calorific value retained by the reformed gas, which is indicated by the right side of Equations (1) and (2), is higher than the calorific value retained by an unreacted substance, which is indicated by the left side of the equations.

Therefore, the heat exchanger 24 can transmit the heat of the exhaust gas passing through the exhaust path 30 to the fuel reforming catalysts 28 and allow the heat to be absorbed in the above reforming reactions. In other words, the system according to the present embodiment can recover the heat of the exhaust gas and convert the reforming fuel to substances ($H_2$ and CO) having a higher calorific value through the use of the recovered heat.

As the calorific value Q2 necessary for the reforming reaction of gasoline is extremely high, it is necessary, for instance, that the fuel reforming catalysts 28 be heated to a temperature of 600° C. or higher to induce the reforming reaction. While the internal combustion engine 10 is operating, therefore, the reforming reaction of ethanol consistently occurs over a large operating region, whereas the reforming reaction of gasoline efficiently occurs, for instance, in a high-rotation-speed, high-load operating region only where exhaust temperature is increased.

The reformed gas derived from the above reforming reactions mixes with the exhaust gas to become the EGR gas. The EGR gas flows back into the intake pipe 12 through the EGR path 32 and mixes with intake air. In this instance, the ECU 50 uses the flow regulating valve 38 to control the rate at which the EGR gas flows back into the intake pipe 12. The EGR gas then flows into the cylinders of the internal combustion engine 10 together with the intake air, and $H_2$ and CO in the reformed gas burn in the cylinders together with the fuel injected from the main fuel injection valve 18.

In the above instance, as described earlier, the calorific value of the reformed gas is higher than that of the original fuel by the amount of exhaust gas heat recovered by the heat exchanger 24. Therefore, when the reformed gas burns in the internal combustion engine 10, the system's overall thermal efficiency increases. This makes it possible to improve the fuel efficiency of the internal combustion engine 10. Further, the heat exchanger 24 can heat the fuel reforming catalysts 28 by using the exhaust gas heat even when a dedicated heating device for the catalysts and heating energy are unavailable. This makes it possible to configure an exhaust heat recovery type system that exhibits high operating efficiency.

Furthermore, reforming EGR control can be exercised to produce an enhanced EGR (Exhaust Gas Recirculation) effect by allowing the EGR gas containing the reformed gas to flow back into an intake system. In general, the rate of EGR has an upper limit because combustion instability results when the EGR rate is raised. On the other hand, when reforming EGR control is exercised, the EGR gas contains a combustible gas. Therefore, a good combustion state can be maintained by exercising reforming EGR control. This makes it possible to raise the upper limit on the EGR rate.

Moreover, the present embodiment uses the upstream air-fuel ratio sensor 58 and downstream air-fuel ratio sensor 60 to detect the concentration of hydrogen in the EGR gas and uses the detection result and the flow rate of the EGR gas to calculate the amount of reformed gas generation. The calculated amount of reformed gas generation is then reflected, for instance, in the next operating conditions such as a reforming fuel injection amount, main fuel injection amount, ignition timing, and EGR valve (flow regulating valve 38) opening. Therefore, the present embodiment makes it possible to exercise proper feedback control over the reformed gas generation amount in accordance, for instance, with the operating status of the internal combustion engine.

(Upstream Air-Fuel Ratio Sensor Structure)

The air-fuel ratio sensors 58, 60 for detecting the concentration of hydrogen will now be described. First of all, the upstream air-fuel ratio sensor 58 will be described. The upstream air-fuel ratio sensor 58 is composed of a common air-fuel ratio sensor that uses, for instance, zirconia. The upstream air-fuel ratio sensor 58 is installed in the exhaust pipe 20 of the internal combustion engine and positioned upstream of the fuel reforming catalysts 28 with respect to the flow direction of the exhaust gas.

The upstream air-fuel ratio sensor 58 detects the concentration of oxygen in the exhaust gas and outputs an upstream sensor signal representing the detected oxygen concentration. The upstream sensor signal is used not only for air-fuel ratio feedback control by the ECU 50 but also for a later-described hydrogen concentration detection process.

FIG. 2 is a cross-sectional view of the upstream air-fuel ratio sensor 58. As shown in the figure, the upstream air-fuel ratio sensor 58 includes a detection element 58A, which is shaped, for instance, like a flat plate; two electrodes 58B, 58C; a diffusion layer 58D, which serves as limitation means; and a housing 58E.

The detection element 58A is made of a solid electrolyte such as zirconia ($ZrO_2$). The electrodes 58B, 58C are mounted respectively on one side surface and on an additional side surface of the detection element 58A to face each other with the detection element 58A in between. One side surface of the detection element 58A, which faces the electrode 58B, is placed at a position that may come into contact with the exhaust gas. The additional side surface of the detection element 58A, which faces the electrode 58C, is placed at a position that is always in contact with atmospheric air.

The diffusion layer 58D is positioned so as to shield one side surface of the detection element 58A from the exhaust gas in coordination with the housing 58D. The diffusion layer 58D is made, for instance, of a permeable porous material. Therefore, the exhaust gas outside the sensor is supplied to one side surface of the detection element 58A through the diffusion layer 58D. However, the rate of such exhaust gas supply is limited in accordance with the permeability (or density) of the diffusion layer 58D.

When a voltage is applied between the electrodes 58B, 58C during an operation of the upstream air-fuel ratio sensor 58, an ion current, which uses oxygen ions as carriers, flows in the detection element 58A. In this instance, the amount of oxygen supplied from the exhaust gas to one side surface of the detection element 58A is limited by the diffusion layer 58D. The ion current then becomes saturated at a current value that corresponds to the oxygen concentration difference between the exhaust gas, which comes into contact with one side surface of the detection element 58A, and the atmospheric air, which comes into contact with the additional side surface of the detection element 58A. The upstream sensor signal is output in accordance with the saturated current value and linearly varies with the concentration of oxygen in the exhaust gas.

(Downstream Air-Fuel Ratio Sensor Structure)

The downstream air-fuel ratio sensor 60 will now be described. As shown in FIG. 1, the downstream air-fuel ratio sensor 60 is installed in the EGR path 32 of the internal combustion engine and positioned downstream of the fuel reforming catalysts 28 with respect to the flow direction of the exhaust gas. Therefore, the downstream air-fuel ratio sensor 60 is exposed to the hydrogen-containing reformed gas during reforming EGR control.

FIG. 3 is a cross-sectional view of the downstream air-fuel ratio sensor 60. As shown in the figure, the downstream air-fuel ratio sensor 60, which is composed of an air-fuel ratio sensor that uses zirconia and is substantially the same as the upstream air-fuel ratio sensor 58, includes a detection element 60A, electrodes 60B, 60C, a diffusion layer 60D, and a housing 60E.

Zirconia has sensitivity for oxygen concentration detection. However, this sensitivity is affected by hydrogen that exists around the sensor. More specifically, if hydrogen exists, the amount of oxygen passing through the diffusion layer is limited depending on the concentration of hydrogen. Consequently, the oxygen ion current flowing in zirconia decreases with an increase in the hydrogen concentration.

As a result, the output generated from the air-fuel ratio sensor while hydrogen exists deviates from the output generated in a reference state where no hydrogen exists so that the oxygen concentration is lowered (to provide a richer air-fuel ratio). Thus, the present embodiment can detect the hydrogen concentration with the air-fuel ratio sensor by determining the amount of such deviation.

When exposed to the EGR gas containing the reformed gas (hydrogen), the downstream air-fuel ratio sensor 60 outputs a downstream sensor signal, which varies with the concentrations of oxygen and hydrogen in the EGR gas, in accordance with the principles described above. On the other hand, the upstream air-fuel ratio sensor 58 does not expose itself to hydrogen. Therefore, the upstream sensor signal varies with the concentration of oxygen only. As such being the case, the present embodiment is configured to detect the hydrogen concentration by using the upstream sensor signal and downstream sensor signal.

A comparison between oxygen and hydrogen reveals that hydrogen molecules are more likely to pass through the diffusion layer 60D than oxygen molecules because the hydrogen molecules are of lower molecular weight than the oxygen molecules. Therefore, the sensor signals respond to a change in the hydrogen concentration to a greater extent than to a change in the oxygen concentration. If the ratio of a sensor signal change to a concentration change (change ratio) is defined as the sensor sensitivity, the air-fuel ratio sensors have higher sensitivity for hydrogen concentration detection than for oxygen concentration detection.

Meanwhile, the output range of the air-fuel ratio sensors, which are configured for oxygen concentration detection, is set to cover a practical range of oxygen concentration variation. Therefore, when an attempt is made to detect the hydrogen concentration with the air-fuel ratio sensors, the output range is not enough to cover a sensor signal that varies to a greater extent than in the case of oxygen concentration detection. In other words, when the hydrogen concentration is higher than a certain level, concentration detection is unachievable due to sensor signal saturation.

In view of the above circumstances, the present embodiment is intentionally configured to set a lower sensitivity for the downstream air-fuel ratio sensor 60 than for the upstream air-fuel ratio sensor 58 so that a sensor signal value generated upon hydrogen concentration detection fits within the output range.

More specifically, the electrode 60B of the downstream air-fuel ratio sensor 60 is smaller than the electrode 58B of the upstream air-fuel ratio sensor 58. Therefore, the electrodes 60B, 60C of the downstream air-fuel ratio sensor have a smaller opposing surface area than the electrodes 58B, 58C of the upstream air-fuel ratio sensor.

Because of the use of the above-described electrode structure, the ion current flowing in the detection element 60A of the downstream air-fuel ratio sensor 60 is smaller than that in the detection element of the upstream air-fuel ratio sensor 58 by the opposing surface area difference between the electrodes 58B, 58C of the upstream air-fuel ratio sensor and the electrodes 60B, 60C of the downstream air-fuel ratio sensor. This decreases the value of the downstream sensor signal for a given hydrogen concentration. Therefore, the ratio of a downstream sensor signal change to a concentration change decreases, thereby making it possible to detect richer oxygen concentrations.

In other words, the sensitivity of the downstream air-fuel ratio sensor 60 can be decreased in accordance with the opposing surface area difference between the electrodes. This ensures that the range of downstream sensor signal variation with hydrogen concentration matches the sensor output range. Consequently, it is possible to prevent the downstream sensor signal from becoming saturated due to an excessively narrow output range and consistently detect a wide range of hydrogen concentration.

(Oxygen Concentration Detection Process)

Figure 4:
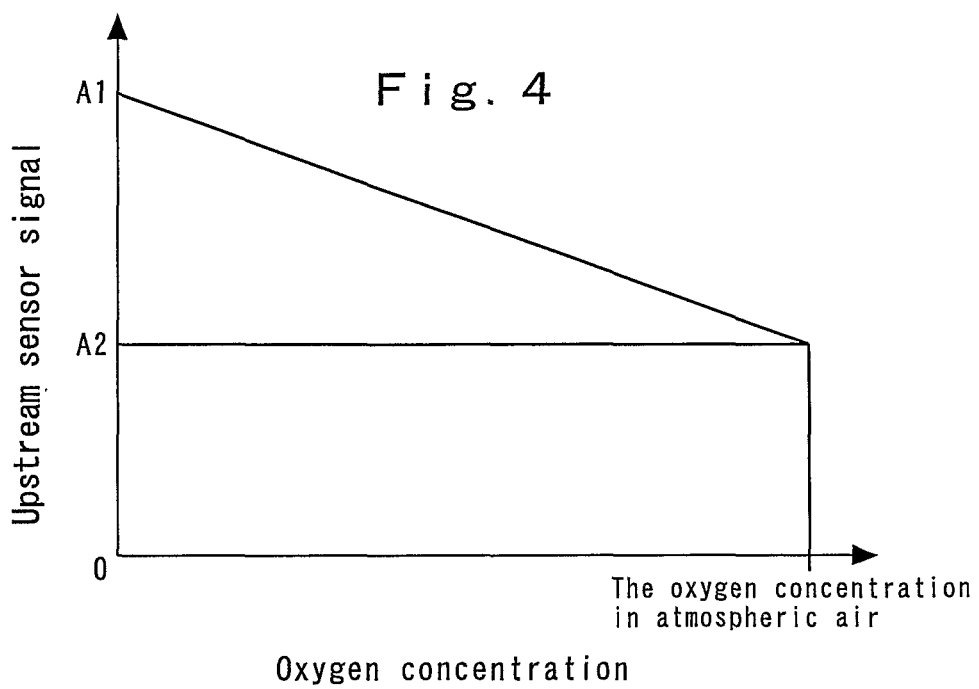
FIG. 4 is a characteristic diagram to show the output characteristic of the upstream sensor signal with respect to oxygen concentration changes.

FIG. 4 shows the output characteristic of the upstream sensor signal with respect to oxygen concentration changes. A saturated current generated in zirconia in accordance with oxygen concentration is converted to a linear voltage signal by a signal processing circuit or the like. This voltage signal is output as an upstream sensor signal that is shown in FIG. 4. Characteristic curve data of the upstream sensor signal is stored beforehand in the ECU 50.

Thus, the ECU 50 can detect the oxygen concentration by referencing the characteristic curve data through the use of the upstream sensor signal. The oxygen concentration detected in the above manner is used not only for air-fuel ratio feedback control by the ECU 50 but also for the hydrogen concentration detection process described below.

(Hydrogen Concentration Detection Process)

Figure 5:
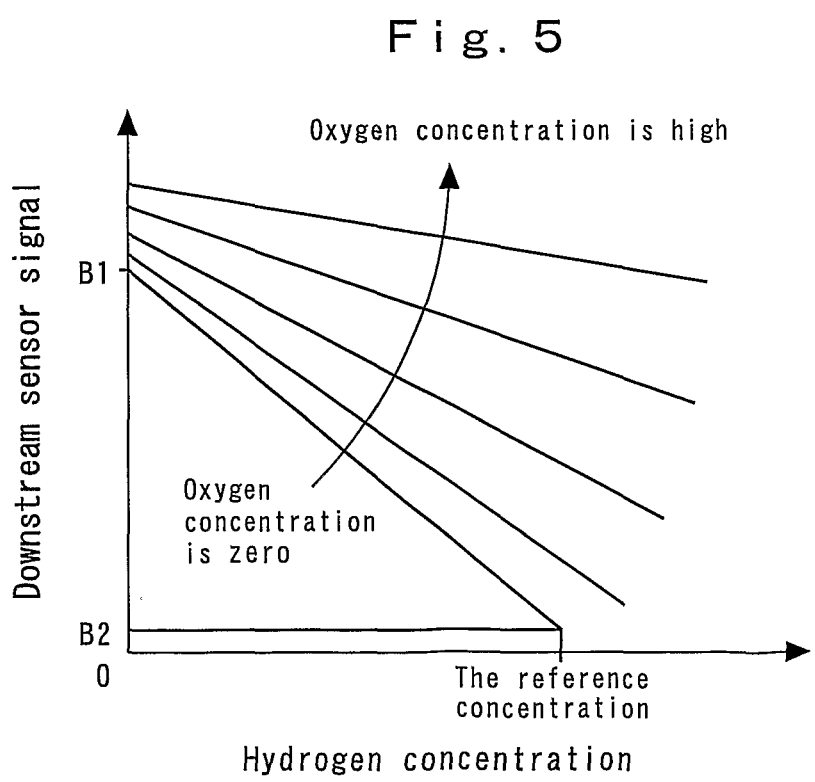
FIG. 5 is a characteristic diagram to show the output characteristic of the downstream sensor signal with respect to changes in the hydrogen concentration and oxygen concentration.

FIG. 5 shows the output characteristic of the downstream sensor signal with respect to changes in the hydrogen concentration and oxygen concentration. A plurality of characteristic curves (characteristic curve data) shown in FIG. 5 indicate the relationship between hydrogen concentration and downstream sensor signal at various oxygen concentrations.

The downstream sensor signal linearly varies with the concentrations of oxygen and hydrogen. More specifically, each characteristic curve data in FIG. 5 indicates that the downstream sensor signal linearly varies with the hydrogen concentration while the oxygen concentration remains unchanged. Therefore, when apiece of characteristic curve data shown in FIG. 5 is selected in accordance with the oxygen concentration detected by the upstream air-fuel ratio sensor 58, the hydrogen concentration can be detected from the downstream sensor signal in accordance with the selected characteristic curve data.

Figure 6:
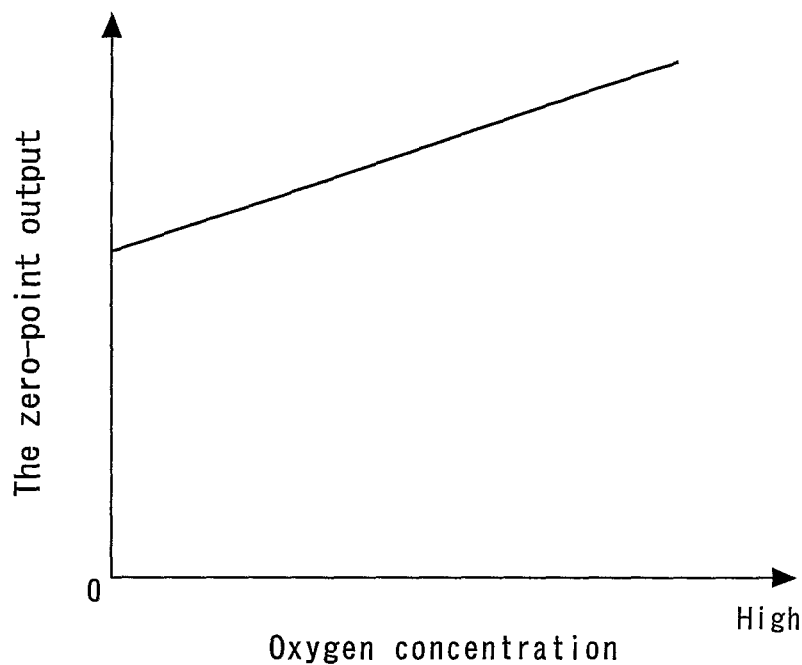
FIG. 6 is a characteristic diagram to show the relationship between the oxygen concentration and a zero-point output that is the intercept of individual characteristic curve date in FIG. 5.

FIG. 6 shows the relationship between the oxygen concentration and a zero-point output that is the intercept of individual characteristic curve data. The zero-point output is defined as a downstream sensor signal value that prevails when the hydrogen concentration is zero. As shown in FIG. 6, the zero-point output of characteristic curve data linearly increases with an increase in the oxygen concentration.

Figure 7:
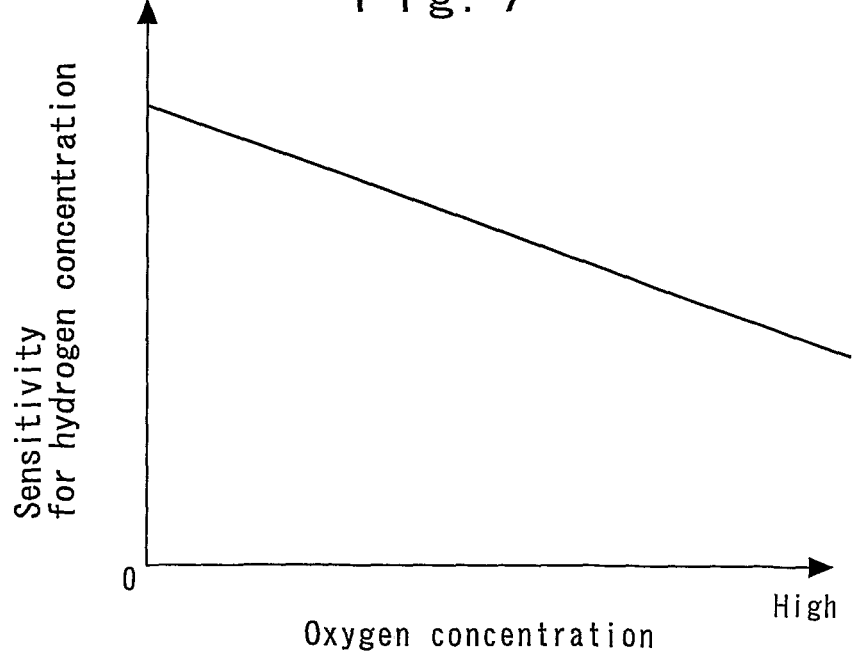
FIG. 7 is a characteristic diagram to show the relationship between the oxygen concentration and a change ratio that is the gradient of individual characteristic curve date shown in FIG. 5.

FIG. 7 shows the relationship between the oxygen concentration and a change ratio that is the gradient of individual characteristic curve data. The change ratio denotes the ratio of a sensor signal value change to a hydrogen concentration change, and corresponds to the sensitivity for hydrogen concentration detection as described earlier. In the present embodiment, the ratio of a change in the characteristic curve data is indicated by a minus value; therefore, FIG. 7 shows the absolute value of a change ratio. As shown in FIG. 7, the characteristic curve data change ratio linearly decreases with an increase in the oxygen concentration and gradually becomes moderate.

The data shown in FIGS. 6 and 7 are stored beforehand in the ECU 50. When performing the hydrogen concentration detection process, the ECU 50 first references the data shown in FIGS. 6 and 7 by using the oxygen concentration detected by the upstream sensor signal, and then acquires the zero-point output and change ratio of characteristic curve data that prevail at the detected oxygen concentration.

Next, the ECU 50 uses the acquired zero-point output and change ratio to set characteristic curve data indicative of the relationship between the downstream sensor signal and hydrogen concentration that prevails at the detected oxygen concentration. For example, the acquired zero-point output and change ratio are used to determine a function expression of characteristic curve data that corresponds to the detected oxygen concentration.

The characteristic curve data corresponds to characteristic curve data that is corrected in accordance with the oxygen concentration. It is obtained by correcting the influence of oxygen concentration, which is contained in the downstream sensor signal, in accordance with the upstream sensor signal. Therefore, the hydrogen concentration prevailing at an arbitrary oxygen concentration can be accurately detected by calculating the hydrogen concentration from the downstream sensor signal in accordance with the characteristic curve data.

In the hydrogen concentration detection process, the downstream sensor signal should be corrected in accordance with the upstream sensor signal so that the downstream sensor signal value corresponds to the hydrogen concentration at an arbitrary oxygen concentration. The method of making such a correction is not limited to the one described in the present embodiment.

According to the present embodiment, the oxygen concentration and hydrogen concentration are reflected in the downstream sensor signal as described earlier. Therefore, the influence of oxygen concentration is eliminated from the downstream sensor signal when the downstream sensor signal is corrected by using the upstream sensor signal in which only the oxygen concentration is reflected. Thus, the hydrogen concentration can be accurately determined in accordance with the corrected downstream sensor signal.

Therefore, when an oxygen detection capability of zirconia or the like and a function for varying the oxygen detection capability in accordance with the hydrogen concentration are used, the hydrogen concentration can be detected easily and accurately simply by mounting the two common air-fuel ratio sensors 58, 60 in the system. Further, the amount of combustible gas generation can be calculated with high accuracy in accordance with the result of hydrogen concentration detection.

Consequently, the system for detecting the hydrogen concentration (combustible gas generation amount) can be established through the use of the small-size, inexpensive air-fuel ratio sensors 58, 60 without having to use a dedicated hydrogen concentration sensor or the concentration of carbon monoxide. Thus, it is possible to facilitate system downsizing and cost reduction. Further, as the upstream air-fuel ratio sensor 58 can be used to correct the influence of oxygen concentration, it is possible to certainly prevent the oxygen concentration from decreasing the accuracy of hydrogen concentration detection and provide consistent detection accuracy.

Further, the present embodiment enables an air-fuel ratio sensor used for the air-fuel ratio feedback control in the internal combustion engine 10 to double as the upstream air-fuel ratio sensor 58 for hydrogen concentration detection. This makes it possible to minimize an increase in the number of sensors and other parts, thereby contributing to further system simplification and cost reduction even when the two air-fuel ratio sensors 58, 60 are used for hydrogen concentration detection.

Furthermore, in the hydrogen concentration detection process performed by the ECU 50, the use of the data shown in FIGS. 6 and 7 makes it possible to acquire the zero-point output and change ratio of characteristic curve data in accordance with the oxygen concentration. Therefore, the use of a linear sensor output makes it possible to accurately set the characteristic curve data by using its zero-point output and change ratio. Since the oxygen concentration is reflected in the characteristic curve data, which is set as described above, the characteristic curve data can be properly corrected in accordance with the oxygen concentration.

(Pressure-Dependent Correction Process)

The air-fuel ratio sensors 58, 60 are constructed so that the sensitivity for oxygen concentration detection varies with the rate at which oxygen molecules pass through the diffusion layers 58D, 60D. Further, the degree of influence of hydrogen concentration on the oxygen detection capability varies with the rate at which hydrogen molecules pass through the diffusion layers 58D, 60D. These molecule passage rates vary with the pressure of the exhaust gas (EGR gas). As such being the case, the present embodiment is configured so as to make sensor signal corrections in accordance with the pressure detected by the pressure sensor 56.

Figure 8:
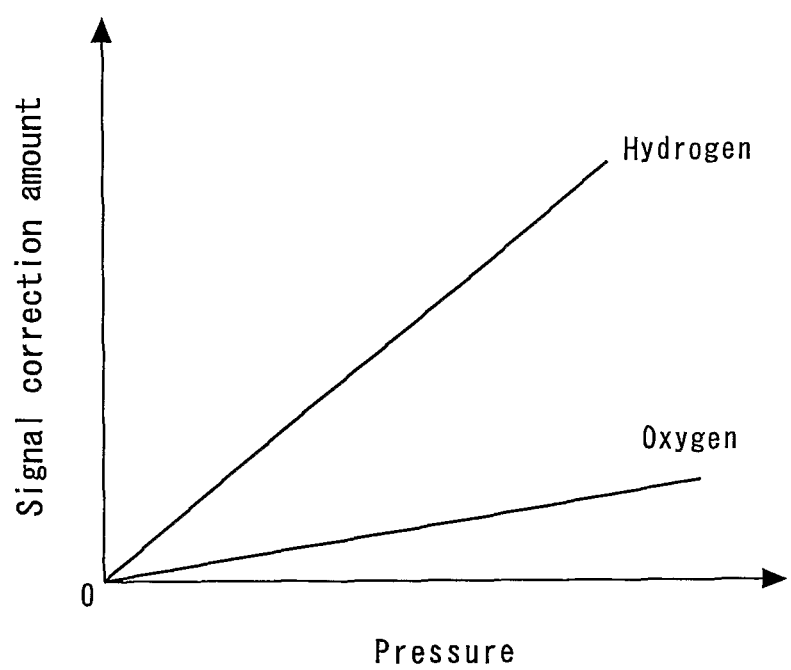
FIG. 8 is a characteristic diagram to show the relationship between exhaust gas (EGR gas) pressure and signal correction amount.

FIG. 8 shows the relationship between exhaust gas pressure and signal correction amount. The data shown in FIG. 8 is stored beforehand in the ECU 50. The rates at which the oxygen molecules and hydrogen molecules pass through the diffusion layers 58D, 60D increase with an increase in the pressure. As a result, the ion currents flowing in the detection elements 58A, 60A increase with an increase in the pressure. Therefore, when the pressure increases, the sensor signals change in the direction of increasing the detected concentration (in the direction of decreasing the sensor signal value shown in FIG. 5).

As such being the case, the signal correction amount for the sensor signals is set so that the signal correction amount increases (the detected concentration decreases) with an increase in the pressure. In other words, the sensitivities of the air-fuel ratio sensors 58, 60 increase with an increase in the exhaust gas pressure. Therefore, a pressure-dependent correction process is performed to make sensor signal corrections so that apparent sensitivities decrease with an increase in the pressure.

Further, a change in the exhaust gas pressure changes the rates at which the molecules pass through the diffusion layers 58D, 60D. The degree of the influence of such a pressure change is greater on hydrogen than on oxygen because hydrogen has a lower molecular weight than oxygen. Therefore, setup is performed so that the ratio of a change in the signal correction amount to a change in the pressure is higher for hydrogen molecules than for oxygen molecules.

When the oxygen concentration and hydrogen concentration are to be detected, the pressure-dependent correction process, which is configured as described above, is performed to detect the pressure of the exhaust gas with the pressure sensor 56 and reference the data shown in FIG. 8 through the use of the detected pressure. This makes it possible to acquire an oxygen concentration signal correction amount and hydrogen concentration signal correction amount for the exhaust gas pressure.

Next, the upstream sensor signal value is corrected in accordance with the pressure by, for instance, adding the oxygen concentration signal correction amount to the upstream sensor signal value or multiplying the upstream sensor signal value by the oxygen concentration signal correction amount. The corrected upstream sensor signal is then used to perform the oxygen concentration detection process described earlier. Similarly, the downstream sensor signal value can be corrected in accordance with the pressure by reflecting the hydrogen concentration signal correction amount in the downstream sensor signal value. The corrected downstream sensor signal is then used to perform the hydrogen concentration detection process described earlier.

As described above, the pressure-dependent correction process makes it possible to correct the sensor signals by the amount of pressure-dependent sensitivity change in the air-fuel ratio sensors 58, 60. Thus, the influence of pressure can be eliminated from the sensor signals. Consequently, even when the exhaust gas pressure changes in accordance, for instance, with the operating status of the internal combustion engine, the system according to the present embodiment can accurately detect the oxygen concentration and hydrogen concentration without being affected by such a change in the exhaust gas pressure.

(Calibration Process for Oxygen)

The output characteristics of air-fuel ratio sensors may deviate from predefined output characteristics due, for instance, to sensor deterioration. Therefore, when the upstream air-fuel ratio sensor 58 and downstream air-fuel ratio sensor 60 are to be operated, they are subjected to an output characteristic calibration process.

The calibration process for oxygen will now be described. This calibration process is performed on both the upstream air-fuel ratio sensor 58 and downstream air-fuel ratio sensor 60. However, the subsequent description deals with the upstream air-fuel ratio sensor 58 as an example. A zero-point reference value and atmospheric air reference value for the oxygen calibration process are stored beforehand in the ECU 50.

The zero-point reference value is a sensor signal value that is similar, for instance, to signal value A1 in FIG. 4 and output from an output-calibrated air-fuel ratio sensor while the oxygen concentration is zero. The atmospheric air reference value is a sensor signal value that is similar, for instance, to signal value A2 in FIG. 4 and output from an output-calibrated air-fuel ratio sensor while a known oxygen concentration (approx. 21%) prevails in atmospheric air.

The calibration process is started by allowing the ECU 50 to adjust the fuel injection amount for the purpose of enriching the air-fuel ratio of the exhaust gas. An oxygen-free exhaust gas is then supplied to the upstream air-fuel ratio sensor 58. In this state, the ECU 50 detects the difference between the upstream sensor signal value and zero-point reference value as the amount of deviation at the zero point.

Next, the injection of fuel from the injection valves 18, 34 is stopped to supply atmospheric air to the upstream air-fuel ratio sensor 58. In this state, the ECU 50 detects the difference between the upstream sensor signal value and atmospheric air reference value as the amount of deviation at an atmospheric oxygen concentration.

As shown in FIG. 4, the output characteristic of the upstream sensor signal is linear with respect to the oxygen concentration. Therefore, the ECU 50 uses the amounts of deviation at two points, namely, at the zero point and at the atmospheric oxygen concentration, to calibrate, for instance, the zero-point output and change ratio of characteristic curve data stored in the ECU 50. This calibration is effected so that the output characteristic of the upstream sensor signal agrees with a predefined output characteristic. In this instance, the result of calibration is stored, for instance, in a nonvolatile memory of the ECU 50 as learning data for calibrating an individual sensor error or the like.

Similarly, the calibration process described above is also performed on the downstream air-fuel ratio sensor 60. The downstream air-fuel ratio sensor 60 is calibrated while the injection of reforming fuel is stopped with the flow regulating valve 38 opened to supply atmospheric air to the EGR path 32.

As described above, when the oxygen calibration process is performed, the air-fuel ratio sensors 58, 60 can be output-calibrated easily and accurately with respect to the oxygen concentration. In this instance, the present embodiment can adjust the oxygen concentration prevailing around the sensors in accordance, for instance, with the fuel injection amount (air-fuel ratio) to readily produce an oxygen-free state and atmospheric air supply state in which sensor output calibration can be effected.

Consequently, even when the air-fuel ratio sensors 58, are deteriorated, the present embodiment can continuously detect the oxygen concentration with high accuracy. In addition, when the accuracy of oxygen concentration detection is increased, the accuracy of hydrogen concentration detection can also be increased because hydrogen concentration detection is based on oxygen concentration detection.

(Calibration Process for Hydrogen)

The calibration process for hydrogen will now be described. This calibration process is performed on the downstream air-fuel ratio sensor 60. A zero-point reference value and nonzero-point reference value for the hydrogen calibration process are stored beforehand in the ECU 50.

The zero-point reference is a sensor signal value that is similar, for instance, to signal value B1 in FIG. 5 and output from an output-calibrated air-fuel ratio sensor while the oxygen concentration and hydrogen concentration are both zero. The nonzero-point reference value is a sensor signal value that is similar, for instance, to signal value B2 in FIG. 5 and output from an output-calibrated air-fuel ratio sensor while the oxygen concentration is zero with the hydrogen concentration adjusted to a predefined reference concentration.

In this instance, the reference concentration is achieved in the calibration process when adjustments are made to place parameters affecting the hydrogen concentration in a predefined error detection state. The parameters include, for instance, a reforming fuel supply amount, exhaust gas flow rate, pressure, and temperature. The exhaust gas flow rate, pressure, and temperature can be adjusted in accordance with the operating status of the internal combustion engine.

The calibration process is started by enriching the exhaust gas air-fuel ratio in the above-described manner and stopping the injection of reforming fuel to supply an oxygen-free, hydrogen-free exhaust gas (EGR gas) to the periphery of the downstream air-fuel ratio sensor 60. In this state, the ECU 50 detects the difference between the downstream sensor signal value and zero-point reference value as the amount of deviation at the zero point.

Next, hydrogen of the reference concentration is generated (oxygen-free, predefined hydrogen supply state) by adjusting the operating status of the internal combustion engine to the aforementioned predefined state while keeping the EGR gas in an oxygen-free state. In the resulting state, the ECU 50 detects the difference between the downstream sensor signal value and nonzero-point reference value as the amount of deviation at a nonzero point.

As shown in FIG. 5, the output characteristic of the downstream sensor signal is linear with respect to the hydrogen concentration. Therefore, the ECU 50 uses the amounts of deviation at two points, namely, at the zero point and at the nonzero point, to calibrate, for instance, the zero-point output and change ratio of characteristic curve data stored in the ECU 50. This calibration is effected so that the output characteristic of the downstream sensor signal agrees with a predefined output characteristic. In this instance, the result of calibration is stored in the ECU 50 as learning data.

As described above, the hydrogen calibration process is performed to provide substantially the same operational advantages as the oxygen calibration process. More specifically, the hydrogen calibration process makes it possible to calibrate the output characteristic of the downstream air-fuel ratio sensor 60 easily and accurately with respect to the hydrogen concentration. Consequently, even when the downstream air-fuel ratio sensor 60 is deteriorated, the hydrogen concentration can be continuously detected with high accuracy.

Further, during the calibration process, the hydrogen concentration can be adjusted in accordance with the operating status of the internal combustion engine while the exhaust gas is kept oxygen-free, for instance, through fuel injection. This makes it possible to readily produce an oxygen-free, hydrogen-free state where sensor output calibration can be effected and an oxygen-free, predefined hydrogen supply state.

(Catalyst Diagnosis Process)

As described above, the present embodiment is capable of accurately detecting the concentration of hydrogen that is generated while reforming EGR control is exercised. Therefore, such a capability is used to perform a diagnosis process on the fuel reforming catalysts 28. This catalyst diagnosis process is started by making adjustments to place parameters affecting the hydrogen concentration in a predefined catalyst diagnosis state.

The predefined catalyst diagnosis state is substantially the same as the aforementioned predefined error detection state. The concentration of hydrogen in the reformed gas generated in the predefined catalyst diagnosis state is stored beforehand in the ECU 50 as a diagnosis reference value. The ECU 50 makes adjustments to place, for instance, the operating status of the internal combustion engine in the predefined catalyst diagnosis state, and compares the hydrogen concentration detected in the predefined catalyst diagnosis state against the diagnosis reference value. Thus, a diagnostic check can be performed on the fuel reforming catalysts 28 in accordance with the amount of deviation between the hydrogen concentration in the predefined catalyst diagnosis state and the diagnosis reference value to judge whether the fuel reforming catalysts 28 are operating normally.

The present embodiment can accurately detect the hydrogen concentration with the two air-fuel ratio sensors 58, 60. Therefore, the present embodiment can also run a diagnostic check on the catalysts with high accuracy. This makes it possible to certainly grasp, for instance, the deterioration of the fuel reforming catalysts 28, thereby providing enhanced system reliability.

[Details of Processes Performed to Implement First Embodiment]

Figure 9:
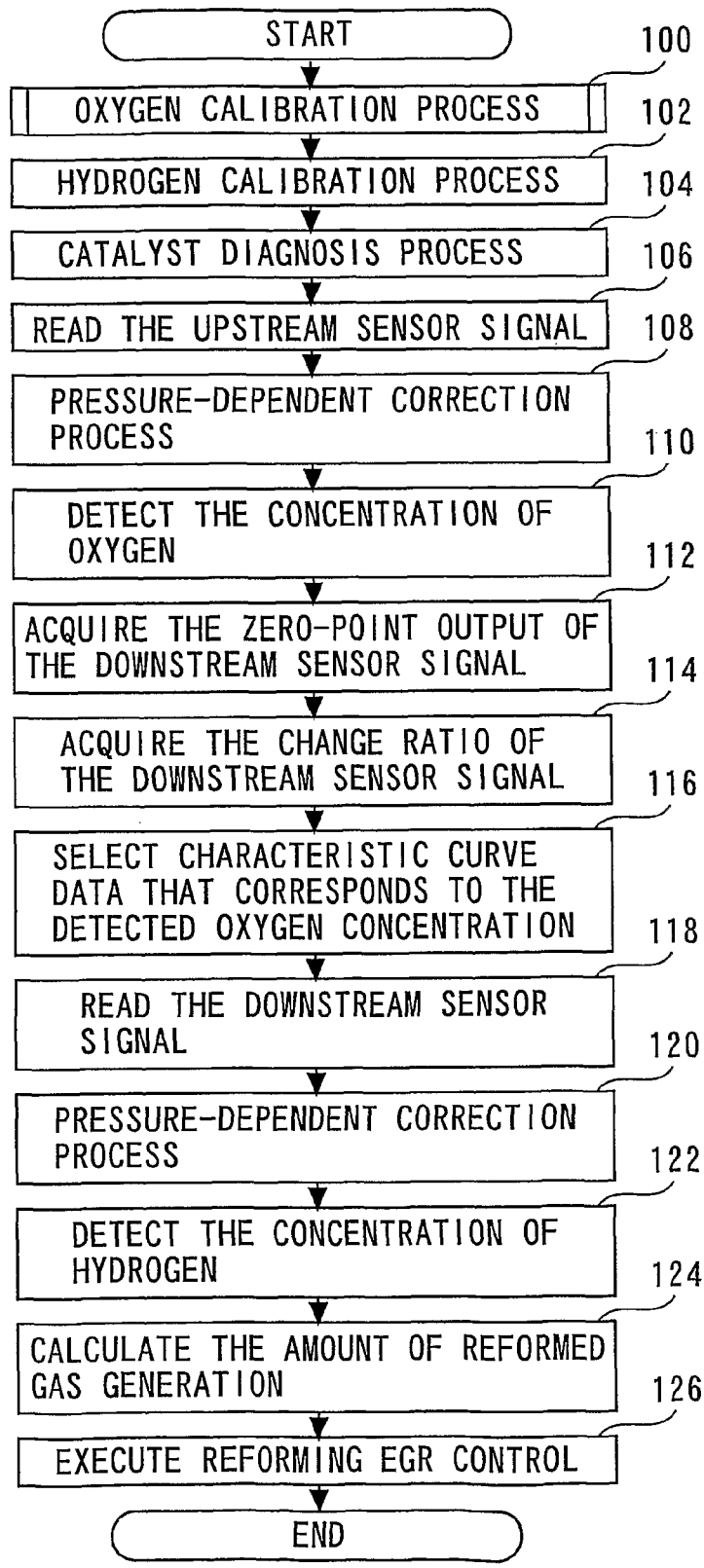
FIG. 9 is a flow chart to show the hydrogen concentration detection process carrying out in the first embodiment.
Figure 10:
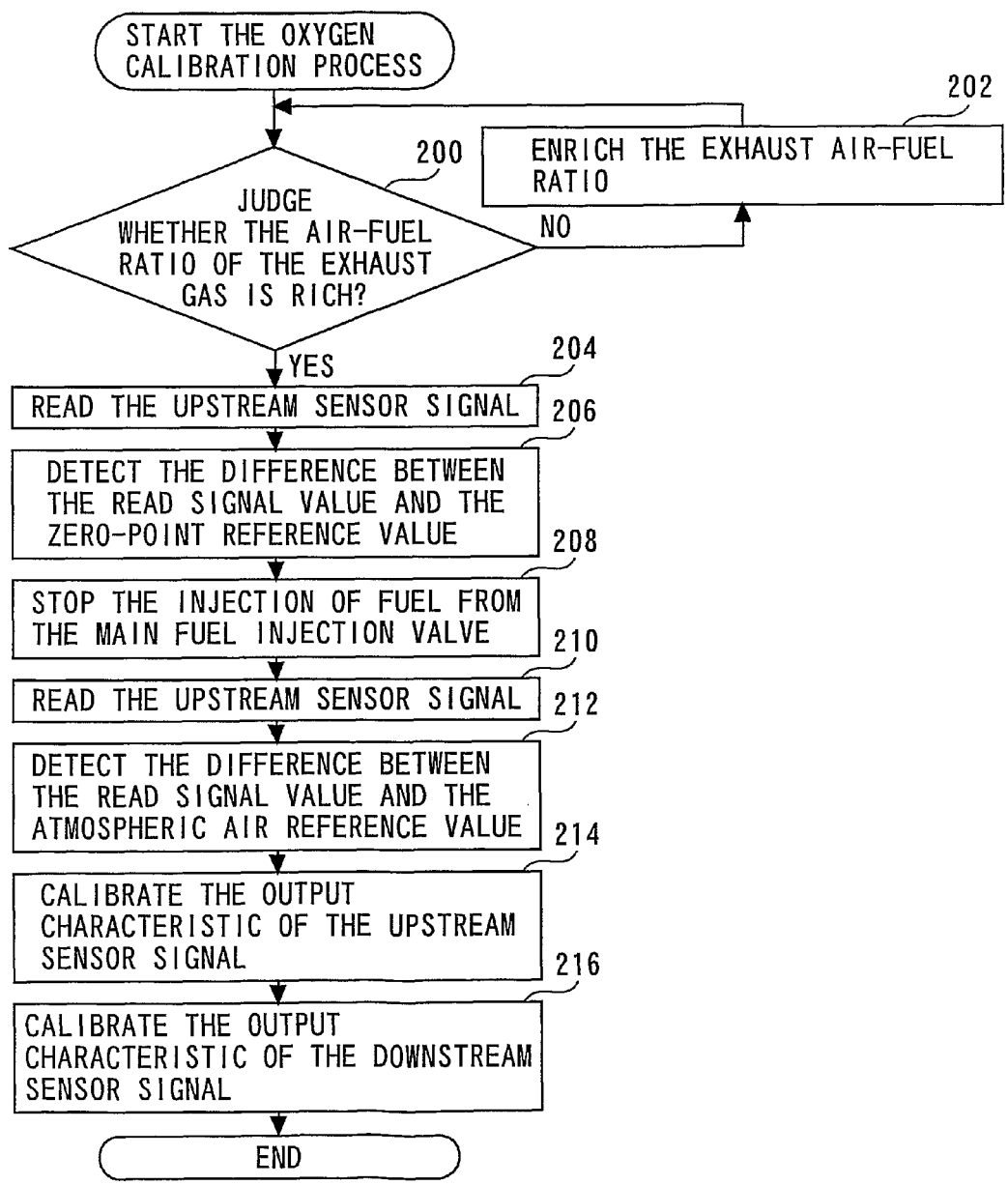
FIG. 10 is a flow chart to show the oxygen calibration process carrying out in the first embodiment.
Figure 11:
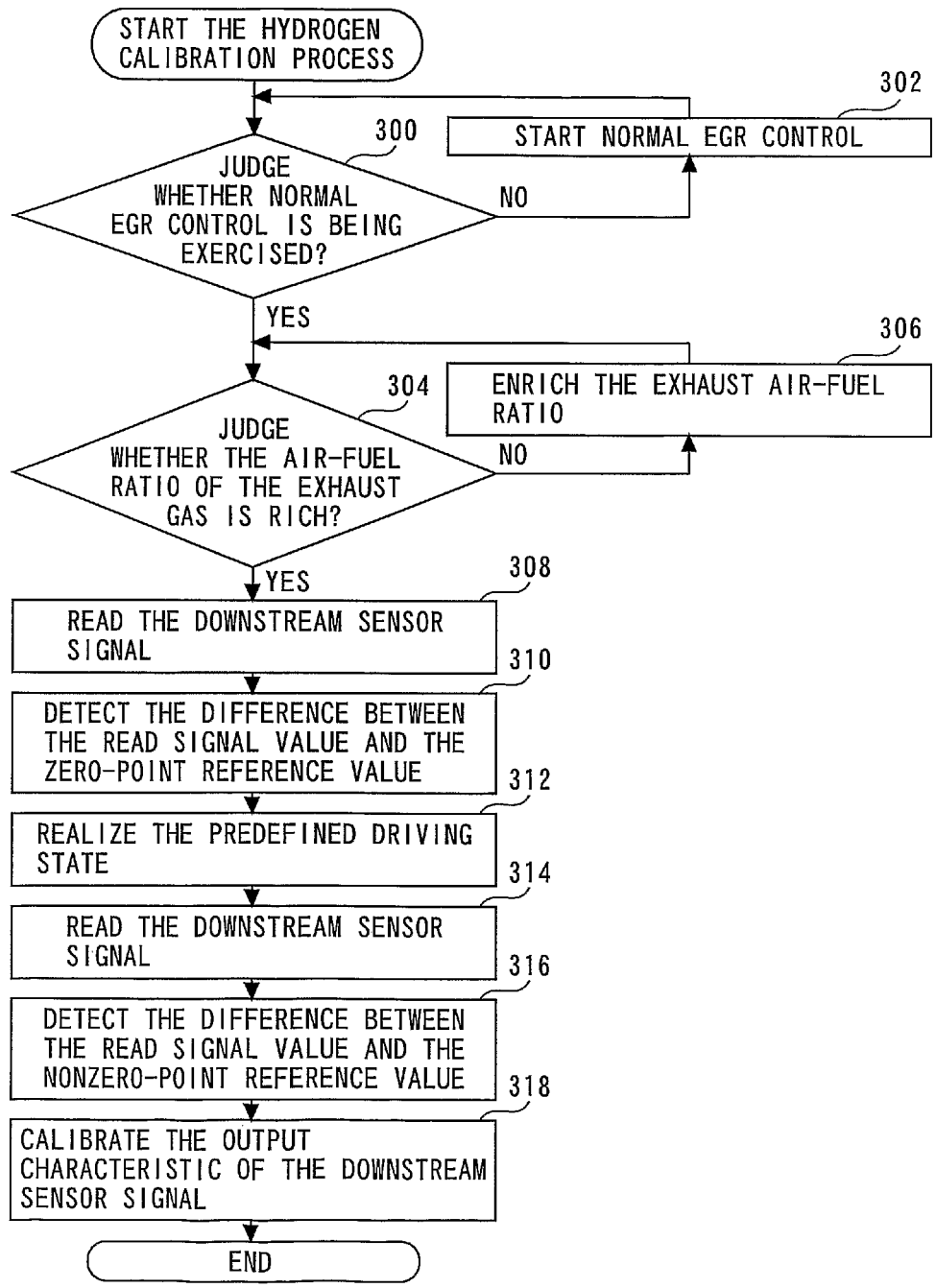
FIG. 11 is a flow chart to show the oxygen calibration process carrying out in the first embodiment.

FIGS. 9 to 11 are flowcharts illustrating routines that the ECU 50 executes to implement system operations in accordance with the present embodiment. The routines shown in these figures are initiated when the internal combustion engine starts up, and repeated at regular intervals.

The hydrogen concentration detection process will now be described with reference to FIG. 9. The hydrogen concentration detection process is started by performing the later-described oxygen calibration process and hydrogen calibration process to calibrate each of the outputs of the air-fuel ratio sensors 58, 60 (steps 100 and 102). In the next step, which is step 104, the previously described catalyst diagnosis process is performed to judge whether the fuel reforming catalysts 28 are normal. If any abnormality is found in the fuel reforming catalysts 28, control is exercised to deal with the abnormality.

Next, step 106 is performed to read the upstream sensor signal. Step 108 is then followed to perform the previously described pressure-dependent correction process on the read signal value. Next, step 110 is performed to reference the data shown in FIG. 4 by using the corrected signal value and detect the concentration of oxygen in the exhaust gas. Further, step 112 is performed to acquire the zero-point output of the downstream sensor signal prevailing at the detected oxygen concentration by referencing the data shown in FIG. 6 through the use of the value of the detected oxygen concentration. Step 114 is then performed similarly to acquire the change ratio of the downstream sensor signal prevailing at the detected oxygen concentration by referencing the data shown in FIG. 7 through the use of the value of the detected oxygen concentration.

Next, step 116 is performed to check each piece of characteristic curve data shown in FIG. 5, select characteristic curve data that corresponds to the detected oxygen concentration, and set, for instance, a function expression for the selected characteristic curve data by using the zero-point output and change ratio. Step 118 is then performed to read the downstream sensor signal. Next, step 120 is followed to perform the pressure-dependent correction process on the value of the read signal. Step 122 is then performed to detect the concentration of hydrogen in the EGR gas by computing, for instance, the function expression for the selected characteristic curve data through the use of the corrected signal value.

Next, step 124 is performed to calculate the flow rate of the EGR gas in accordance, for instance, with the operating status of the internal combustion engine and the degree of opening of the flow regulating valve 38, and calculate the amount of reformed gas generation by using the flow rate and the value of the detected hydrogen concentration. Consequently, step 126 is performed to execute reforming EGR control while feeding back the reformed gas generation amount into the execution of such control.

The oxygen calibration process will now be described with reference to FIG. 10. In the oxygen calibration process, step 200 is first performed to judge whether the air-fuel ratio of the exhaust gas is rich ($\lambda \leq 1$). If the exhaust air-fuel ratio is not rich, step 202 is performed to enrich the exhaust air-fuel ratio, for instance, by adjusting the fuel injection amount.

As a result, an oxygen-free exhaust gas is supplied to the upstream air-fuel ratio sensor 58. In the resulting state, step 204 is performed to read the upstream sensor signal. Step 206 is then performed to detect the difference between the read signal value and the zero-point reference value, which is stored beforehand in the ECU 50, and store the detected difference as the amount of deviation at the zero point.

Next, step 208 is performed to supply atmospheric air to the upstream air-fuel ratio sensor 58 by stopping the injection of fuel from the main fuel injection valve 18. In the resulting state, step 210 is performed to read the upstream sensor signal. Step 212 is then performed to detect the difference between the read signal value and the atmospheric air reference value, which is stored beforehand in the ECU 50, and store the detected difference as the amount of deviation at the atmospheric oxygen concentration.

Next, step 214 is performed to calibrate the output characteristic of the upstream sensor signal by using the amounts of deviation at two points, namely, at the zero point and at the atmospheric oxygen concentration. In a typical example, this calibration process is performed to calibrate, for instance, the zero-point output and change ratio of the characteristic curve data stored in the ECU 50.

Next, step 216 is performed to calibrate the output characteristic of the downstream sensor signal by subjecting the downstream air/fuel ratio sensor 60 to the same calibration process as described in steps 200 to 214. More specifically, the calibration process is started by stopping the injection of reforming fuel and enriching the exhaust air-fuel ratio to supply an oxygen-free, hydrogen-free EGR gas to the downstream air-fuel ratio sensor 60. Then, in the resulting state, the amount of deviation at the aforementioned zero point is detected.

Further, the injection of main fuel and reforming fuel is stopped to supply hydrogen-free atmospheric air to the downstream air-fuel ratio sensor 60. Then, in the resulting state, the amount of deviation at the aforementioned atmospheric oxygen concentration is detected. The output characteristic of the downstream sensor signal can be calibrated by using the amounts of deviation prevailing at the above two points.

The hydrogen calibration process will now be described with reference to FIG. 11. In the hydrogen calibration process, step 300 is first performed to judge whether EGR control in an unreformed state (normal EGR control) is being exercised. If reforming EGR control is being exercised in this instance, it is stopped. If normal EGR control is stopped, it is started to supply a reformed-gas-free exhaust gas to the EGR path 32 (step 302).

Next, step 304 is performed to judge whether the air-fuel ratio of the exhaust gas is rich. If the exhaust gas air-fuel ratio is not rich, step 306 is performed in the same manner as in step 202 to enrich the exhaust gas air-fuel ratio.

As a result, an oxygen-free, hydrogen-free EGR gas is supplied to the downstream air-fuel ratio sensor 60. In the resulting state, step 308 is performed to read the downstream sensor signal. Step 310 is then performed to detect the difference between the read signal value and the zero-point reference value, which is stored beforehand in the ECU 50, and store the detected difference as the amount of deviation at the zero point.

Next, in a state where reforming EGR control is initiated, step 312 is performed to make adjustments to place the parameters, such as the reforming fuel supply amount, exhaust gas flow rate, pressure, and temperature, in the predefined error detection state, which is memorized beforehand in the ECU 50. This ensures that the fuel reforming catalysts 28 supply hydrogen of the reference concentration to the EGR path 32.

In the resulting state, step 314 is performed to read the downstream sensor signal. Step 316 is then performed to detect the difference between the read signal value and the nonzero-point reference value, which is stored beforehand in the ECU 50, and store the detected difference as the amount of deviation at the nonzero point. Next, step 318 is performed in substantially the same manner as in the oxygen calibration process to calibrate the output characteristic of the downstream sensor signal by using the amounts of deviation at two points, namely, at the zero point and at the nonzero point.

As described in detail above, the present embodiment can accurately detect the hydrogen concentration during reforming EGR control by using the two air-fuel ratio sensors 58, 60, and properly control the amount of reformed gas generation in accordance with the detection result.

Second Embodiment

Figure 12:
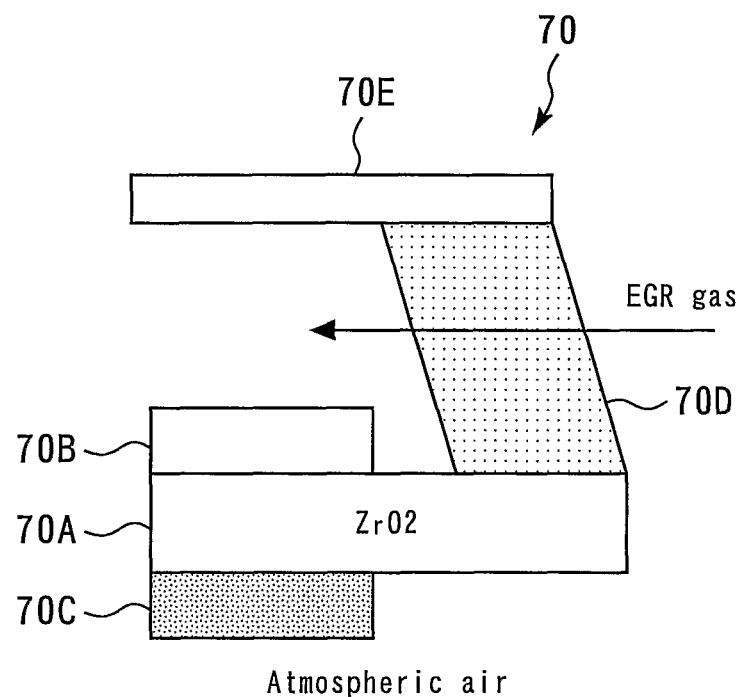
FIG. 12 is a cross-sectional view as FIG. 3 to show the downstream air-fuel ration sensor of a fuel reforming apparatus according the second embodiment.

A second embodiment of the present invention will now be described with reference to FIG. 12. The second embodiment uses the same system configuration (FIG. 1) as the first embodiment, but differs from the first embodiment in the structure of the downstream air-fuel ratio sensor.

The downstream air-fuel ratio sensor 70 according to the second embodiment is similar to the counterpart according to the first embodiment in that the former includes a detection element 70A, electrodes 70B, 70C, a diffusion layer 70D, and a housing 70E. However, the diffusion layer 70D is made of a denser material than the diffusion layer 58D of the upstream air-fuel ratio sensor 58. Therefore, the diffusion layer 70D is less permeable than the diffusion layer 58D of the upstream air-fuel ratio sensor 58.

As a result, oxygen and hydrogen are less likely to be supplied to one side surface of the detection element 70A than in the case of the upstream air-fuel ratio sensor 58. This reduces the ion current to be generated in the detection element 70A under the same concentration conditions. As such being the case, the present embodiment is configured so that the sensitivity of the downstream air-fuel ratio sensor 70 is lower than that of the upstream air-fuel ratio sensor 58 by the amount of permeability difference between the diffusion layer 58D and diffusion layer 70D.

Although the present embodiment is configured as described above, it provides substantially the same operational advantages as the first embodiment. Further, in the present embodiment in particular, the downstream air-fuel ratio sensor 70 can be implemented simply by replacing the diffusion layer 58D of the upstream air-fuel ratio sensor 58 with the dense diffusion layer 70D. In this instance, the electrodes 70B, 70C may be identical with those of the upstream air-fuel ratio sensor 58. Therefore, it is easy to form the downstream air-fuel ratio sensor 70 that has limited sensitivity.

In the foregoing embodiments, steps 112 to 122, which are shown in FIG. 9, present a concrete example of the hydrogen concentration detection means; and steps 112 to 116, in particular, present a concrete example of the signal correction means. Further, step 112 presents a concrete example of the zero-point output acquisition means; step 114 presents a concrete example of the change ratio acquisition means; and step 116 presents a concrete example of the characteristic setup means. Furthermore, steps 106 and 110 present a concrete example of the oxygen concentration calculation means; steps 108 and 120 present a concrete example of the pressure-dependent correction means; and step 104 presents a concrete example of the catalyst diagnosis means.

Further, referring to FIG. 10, steps 200, 202, and 208 present a concrete example of the gaseous material supply means; steps 204 and 206 present a concrete example of the first oxygen error detection means; steps 210 and 212 present a concrete example of the second oxygen error detection means; and step 214 presents a concrete example of the oxygen signal calibration means.

Furthermore, referring to FIG. 11, step 312 presents a concrete example of the adjustment means; steps 308 and 310 present a concrete example of the first hydrogen error detection means; steps 314 and 316 present a concrete example of the second hydrogen error detection means; and step 318 presents a concrete example of the hydrogen signal calibration means.

The configurations employed by the foregoing embodiments are such that the sensitivities of the downstream air-fuel ratio sensors 60, 70 are lowered by reducing the size of the electrode 60B or making the diffusion layer 70D dense. However, the present invention may use an alternative method to lower the sensitivities of the downstream air-fuel ratio sensors. For example, when the employed air-fuel ratio sensors supply a measurement target gaseous material to one side surface of the detection element through a diffusion hole made in the housing, the sensor sensitivities may be lowered by decreasing the diameter of the diffusion hole.

The downstream air-fuel ratio sensor according to the present invention may be constructed by combining any two or all three of the air-fuel ratio sensors 60, 70 according to the first or second embodiment and an air-fuel ratio sensor having the aforementioned small-diameter diffusion hole. For example, the downstream air-fuel ratio sensor may be constructed by using a small-size electrode and forming a dense diffusion layer.

The foregoing embodiments have been described in conjunction with the air-fuel ratio sensors 58, 60, 70 whose signal linearly decreases with an increase in the concentration of a detection target. However, the present invention is not limited to the use of such air-fuel ratio sensors. The present invention may alternatively be configured to use air-fuel ratio sensors whose signal increases with an increase in the concentration or nonlinearly varies with the concentration.

Further, the foregoing embodiments have been described in conjunction with the air-fuel ratio sensors 58, 60, 70 that include the detection element 58A, 60A, or 70A, which is made of zirconia, and the diffusion layer 58D, 60D, or 70D, which is made, for instance, of alumina. However, the present invention is not limited to the use of such air-fuel ratio sensors. For example, an alternative would be to use a detection element and diffusion layer made of materials other than zirconia and alumina as far as they have an oxygen detection capability and a function for varying the oxygen detection sensitivity in accordance with the hydrogen concentration.

Meanwhile, the foregoing embodiments are configured so that the EGR path 32 branches off from the exhaust pipe 20 at an upstream end of the heat exchanger 24. However, the present invention is not limited to such a configuration. An alternative configuration may be employed so that the EGR path 32 branches off from the exhaust pipe 20 at a downstream end of the heat exchanger 24.

Further, the foregoing embodiments are configured so that the upstream air-fuel ratio sensor 58 is mounted in the exhaust pipe 20 and positioned upstream of the heat exchanger 24. However, the mounting position of the upstream air-fuel ratio sensor according to the present invention is not limited to the position described in conjunction with the foregoing embodiments. For example, a portion of the exhaust pipe 20 that is positioned downstream of the heat exchanger 24 is positioned upstream of the fuel reforming catalysts 28. Therefore, the upstream air-fuel ratio sensor 58 may alternatively be mounted in the exhaust pipe 20 and positioned downstream of the heat exchanger 24. Another alternative would be to mount the upstream air-fuel ratio sensor 58 in the EGR path 32 and position it upstream of the fuel reforming catalysts 28.

Similarly, the mounting position of the downstream air-fuel ratio sensor according to the present invention is not limited to the position described in conjunction with the foregoing embodiments. Any mounting position may alternatively be selected for the downstream air-fuel ratio sensor as far as it is positioned downstream of the fuel reforming catalysts 28. For example, the downstream air-fuel ratio sensor 60 may be positioned at a junction between the EGR path 32 and intake pipe 12 or positioned slightly away from the junction and toward the intake pipe 12.

It is assumed that the foregoing embodiments use a fuel mixture of gasoline and ethanol as the reforming fuel. However, the present invention is not limited to the use of such a fuel mixture. For example, a fuel mixture of gasoline and methanol or other alcohol may alternatively be used as the reforming fuel.

Further, the present invention is not limited to the use of an alcohol-containing fuel. Any fuel may be applied to the present invention as far as it contains gasoline. More specifically, the present invention is applicable, for instance, to a fuel composed of gasoline only and a fuel mixture of gasoline and a substance other than alcohol.

Furthermore, it is assumed that the foregoing embodiments heat the fuel reforming catalysts 28 by using the heat of the exhaust gas. However, the present invention does not always need to use the heat of the exhaust gas. For example, the present invention may be applied to an internal combustion engine that is not of an exhaust heat recovery type. More specifically, the present invention may be configured to heat the fuel reforming catalysts 28 by using a heat source (e.g., dedicated heater) other than exhaust gas.

Moreover, the foregoing embodiments have been described on the assumption that the fuel reforming apparatus is applied to the internal combustion engine 10. However, the present invention can be applied not only to internal combustion engines but also to a wide variety of machines and devices that perform fuel reforming.

The invention claimed is:

1. A fuel reforming apparatus comprising:
a fuel reforming catalyst which is positioned in a flow path of a gaseous material containing a reforming fuel and used to generate a hydrogen-containing combustible gas from the reforming fuel;
an upstream air-fuel ratio sensor which is positioned upstream of the fuel reforming catalyst with respect to the flow direction of the gaseous material and used to output an upstream sensor signal representing the concentration of oxygen in the gaseous material;
a downstream air-fuel ratio sensor which is positioned downstream of the fuel reforming catalyst with respect to the flow direction of the gaseous material and used to output a downstream sensor signal representing the concentrations of oxygen and hydrogen in the gaseous material; and
a hydrogen concentration detection unit which uses the upstream sensor signal and the downstream sensor signal to detect the concentration of hydrogen in the gaseous material at a position downstream of the fuel reforming catalyst
wherein the hydrogen concentration detection unit includes a signal correction unit which corrects the influence of the oxygen concentration, which is contained in the downstream sensor signal, in accordance with the upstream sensor signal,
the fuel reforming apparatus further comprising:
an oxygen concentration calculation unit which calculates the oxygen concentration from the upstream sensor signal; and
a storage unit which stores, in advance, characteristic curve data indicative of the relationship between the downstream sensor signal and the hydrogen concentration;
wherein the signal correction unit corrects the characteristic curve data in accordance with the oxygen concentration; and
wherein the hydrogen concentration detection unit uses the corrected characteristic curve data to calculate the hydrogen concentration from the downstream sensor signal.

2. The fuel reforming apparatus according to claim 1, wherein the signal correction unit includes zero-point output acquisition unit which acquires a value of the downstream sensor signal in accordance with the oxygen concentration when the hydrogen concentration is zero; change ratio acquisition unit which acquires the ratio of a change in the downstream sensor signal to a change in the hydrogen concentration in accordance with the oxygen concentration; and characteristic setup unit which sets the characteristic curve data at detected oxygen concentration in accordance with the results of acquisition by the zero-point output acquisition unit and the change ratio acquisition unit.

3. The fuel reforming apparatus according to claim 1, wherein the downstream air-fuel ratio sensor has a lower sensitivity than the upstream air-fuel ratio sensor.

4. The fuel reforming apparatus according to claim 1, wherein the upstream air-fuel ratio sensor and the downstream air-fuel ratio sensor each include a detection element, which is made of a zirconia-containing material and provided with one side surface and an additional side surface; two electrodes, which are mounted respectively on one side surface and on the additional side surface of the detection element to face each other with the detection element in between; and a limitation unit, which is positioned to shield one side surface of the detection element from the gaseous material containing a detection target and limit the rate at which the detection target is supplied to one side surface of the detection element.

5. The fuel reforming apparatus according to claim 4, wherein the electrodes of the downstream air-fuel ratio sensor have a smaller opposing surface area than the electrodes of the upstream air-fuel ratio sensor; and wherein the sensitivity of the downstream air-fuel ratio sensor is lowered in accordance with the opposing surface area difference between the upstream and downstream air-fuel ratio sensors.

6. The fuel reforming apparatus according to claim 4, wherein the limitation unit is a diffusion layer that allows an extraneous gaseous material containing the detection target to pass toward one side surface of the detection element; wherein the diffusion layer of the downstream air-fuel ratio sensor has a lower permeability than the diffusion layer of the upstream air-fuel ratio sensor; and wherein the sensitivity of the downstream air-fuel ratio sensor is lowered in accordance with the permeability difference between the upstream and downstream air-fuel ratio sensors.

7. The fuel reforming apparatus according to claim 1, further comprising:
pressure detection unit which detects the pressure of the gaseous material; and
pressure-dependent correction unit which corrects the value of at least either the upstream sensor signal or the downstream sensor signal in accordance with the pressure of the gaseous material.

8. The fuel reforming apparatus according to claim 7, wherein the pressure-dependent correction unit makes corrections so that the detected concentration of oxygen or hydrogen decreases with an increase in the pressure.

9. The fuel reforming apparatus according to claim 1, further comprising:
a gaseous material supply unit which individually supplies an oxygen-free gaseous material and atmospheric air to at least either the upstream air-fuel ratio sensor or the downstream air-fuel ratio sensor;
a first oxygen error detection unit which detects the amount of deviation between an output signal value of the air-fuel ratio sensor and a predefined zero-point reference value while the oxygen-free gaseous material is supplied to the air-fuel ratio sensor;
a second oxygen error detection unit which detects the amount of deviation between an output signal value of the air-fuel ratio sensor and a predefined atmospheric air reference value while the atmospheric air is supplied to the air-fuel ratio sensor; and
an oxygen signal calibration unit which calibrates the output signal values by using the amounts of deviation from the zero-point reference value and the atmospheric air reference value.

10. The fuel reforming apparatus according to claim 1, further comprising:
a reforming fuel supply unit which supplies the reforming fuel to the fuel reforming catalyst;
a gaseous material supply unit which supplies an oxygen-free gaseous material to the downstream air-fuel ratio sensor;
an adjustment unit which makes adjustments to place parameters affecting the hydrogen concentration in a predefined error detection state;
a first hydrogen error detection unit which detects the amount of deviation between an output signal value of the downstream air-fuel ratio sensor and a predefined zero-point reference value while the supply of reforming fuel is shut off with the oxygen-free gaseous material supplied to the downstream air-fuel ratio sensor;
a second hydrogen error detection unit which detects the amount of deviation between an output signal value of the downstream air-fuel ratio sensor and a predefined nonzero-point reference value while the parameters are adjusted and placed in the predefined state with the oxygen-free gaseous material supplied to the downstream air-fuel ratio sensor; and
a hydrogen signal calibration unit which calibrates the output signal values by using the amounts of deviation from the zero-point reference value and the nonzero-point reference value.

11. The fuel reforming apparatus according to claim 1, further comprising:
a catalyst diagnosis unit which makes adjustments to place parameters affecting the hydrogen concentration in a predefined catalyst diagnosis state and compares a detected hydrogen concentration against a predefined diagnosis reference value to run a diagnostic check on the operation of the fuel reforming catalyst.

12. The fuel reforming apparatus according to claim 1, wherein the upstream air-fuel ratio sensor is used during air-fuel ratio feedback control to regulate the air-fuel ratio in accordance with the concentration of oxygen in an exhaust gas emitted from an internal combustion engine.

13. A fuel reforming apparatus comprising:
a fuel reforming catalyst which is positioned in a flow path of a gaseous material containing a reforming fuel and used to generate a hydrogen-containing combustible gas from the reforming fuel;
an upstream air-fuel ratio sensor which is positioned upstream of the fuel reforming catalyst with respect to the flow direction of the gaseous material and used to output an upstream sensor signal representing the concentration of oxygen in the gaseous material;
a downstream air-fuel ratio sensor which is positioned downstream of the fuel reforming catalyst with respect to the flow direction of the gaseous material and used to output a downstream sensor signal representing the concentrations of oxygen and hydrogen in the gaseous material; and
a hydrogen concentration detection unit which uses the upstream sensor signal and the downstream sensor signal to detect the concentration of hydrogen in the gaseous material at a position downstream of the fuel reforming catalyst;
wherein the downstream air-fuel ratio sensor has a lower sensitivity than the upstream air-fuel ratio sensor.

14. A fuel reforming apparatus comprising:
a fuel reforming catalyst which is positioned in a flow path of a gaseous material containing a reforming fuel and used to generate a hydrogen-containing combustible gas from the reforming fuel;
an upstream air-fuel ratio sensor which is positioned upstream of the fuel reforming catalyst with respect to the flow direction of the gaseous material and used to output an upstream sensor signal representing the concentration of oxygen in the gaseous material;
a downstream air-fuel ratio sensor which is positioned downstream of the fuel reforming catalyst with respect to the flow direction of the gaseous material and used to output a downstream sensor signal representing the concentrations of oxygen and hydrogen in the gaseous material; and
a hydrogen concentration detection unit which uses the upstream sensor signal and the downstream sensor signal to detect the concentration of hydrogen in the gaseous material at a position downstream of the fuel reforming catalyst;
wherein the upstream air-fuel ratio sensor and the downstream air-fuel ratio sensor each include a detection element, which is made of a zirconia-containing material and provided with one side surface and an additional side surface; two electrodes, which are mounted respectively on one side surface and on the additional side surface of the detection element to face each other with the detection element in between; and a limitation unit, which is positioned to shield one side surface of the detection element from the gaseous material containing a detection target and limit the rate at which the detection target is supplied to one side surface of the detection element.

15. The fuel reforming apparatus according to claim 14, wherein the electrodes of the downstream air-fuel ratio sensor have a smaller opposing surface area than the electrodes of the upstream air-fuel ratio sensor; and
wherein the sensitivity of the downstream air-fuel ratio sensor is lowered in accordance with the opposing surface area difference between the upstream and downstream air-fuel ratio sensors.

16. The fuel reforming apparatus according to claim 14, wherein the limitation unit is a diffusion layer that allows an extraneous gaseous material containing the detection target to pass toward one side surface of the detection element; wherein the diffusion layer of the downstream air-fuel ratio sensor has a lower permeability than the diffusion layer of the upstream air-fuel ratio sensor; and wherein the sensitivity of the downstream air-fuel ratio sensor is lowered in accordance with the permeability difference between the upstream and downstream air-fuel ratio sensors.

17. A fuel reforming apparatus comprising:
a fuel reforming catalyst which is positioned in a flow path of a gaseous material containing a reforming fuel and used to generate a hydrogen-containing combustible gas from the reforming fuel;
an upstream air-fuel ratio sensor which is positioned upstream of the fuel reforming catalyst with respect to the flow direction of the gaseous material and used to output an upstream sensor signal representing the concentration of oxygen in the gaseous material;
a downstream air-fuel ratio sensor which is positioned downstream of the fuel reforming catalyst with respect to the flow direction of the gaseous material and used to output a downstream sensor signal representing the concentrations of oxygen and hydrogen in the gaseous material;
a hydrogen concentration detection unit which uses the upstream sensor signal and the downstream sensor signal to detect the concentration of hydrogen in the gaseous material at a position downstream of the fuel reforming catalyst;
a gaseous material supply unit which individually supplies an oxygen-free gaseous material and atmospheric air to at least either the upstream air-fuel ratio sensor or the downstream air-fuel ratio sensor;
a first oxygen error detection unit which detects the amount of deviation between an output signal value of the air-fuel ratio sensor and a predefined zero-point reference value while the oxygen-free gaseous material is supplied to the air-fuel ratio sensor;
a second oxygen error detection unit which detects the amount of deviation between an output signal value of the air-fuel ratio sensor and a predefined atmospheric air reference value while the atmospheric air is supplied to the air-fuel ratio sensor; and
an oxygen signal calibration unit which calibrates the output signal values by using the amounts of deviation from the zero-point reference value and the atmospheric air reference value.

18. A fuel reforming apparatus comprising:
a fuel reforming catalyst which is positioned in a flow path of a gaseous material containing a reforming fuel and used to generate a hydrogen-containing combustible gas from the reforming fuel;
an upstream air-fuel ratio sensor which is positioned upstream of the fuel reforming catalyst with respect to the flow direction of the gaseous material and used to output an upstream sensor signal representing the concentration of oxygen in the gaseous material;
a downstream air-fuel ratio sensor which is positioned downstream of the fuel reforming catalyst with respect to the flow direction of the gaseous material and used to output a downstream sensor signal representing the concentrations of oxygen and hydrogen in the gaseous material;
a hydrogen concentration detection unit which uses the upstream sensor signal and the downstream sensor signal to detect the concentration of hydrogen in the gaseous material at a position downstream of the fuel reforming catalyst;
a reforming fuel supply unit which supplies the reforming fuel to the fuel reforming catalyst;
a gaseous material supply unit which supplies an oxygen-free gaseous material to the downstream air-fuel ratio sensor;

an adjustment unit which makes adjustments to place parameters affecting the hydrogen concentration in predefined error detection state;

a first hydrogen error detection unit which detects the amount of deviation between an output signal value of the downstream air-fuel ratio sensor and a predefined zero-point reference value while the supply of reforming fuel is shut off with the oxygen-free gaseous material supplied to the downstream air-fuel ratio sensor;

a second hydrogen error detection unit which detects the amount of deviation between an output signal value of the downstream air-fuel ratio sensor and a predefined nonzero-point reference value while the parameters are adjusted and placed in the predefined state with the oxygen-free gaseous material supplied to the downstream air-fuel ratio sensor; and a hydrogen signal calibration unit which calibrates the output signal values by using the amounts of deviation from the zero-point reference value and the nonzero-point reference value.

* * * * *